US007056655B2

(12) United States Patent
Cantor

(10) Patent No.: US 7,056,655 B2
(45) Date of Patent: *Jun. 6, 2006

(54) METHODS FOR MONITORING AND GUIDING THERAPEUTIC SUPPRESSION OF PARATHYROID HORMONE IN RENAL PATIENTS HAVING SECONDARY HYPERPARATHYROIDISM

(75) Inventor: Thomas L. Cantor, El Cajon, CA (US)

(73) Assignee: Scantibodies Laboratory, Inc., Santee, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/286,465

(22) Filed: Nov. 1, 2002

(65) Prior Publication Data

US 2003/0157560 A1 Aug. 21, 2003

Related U.S. Application Data

(63) Continuation-in-part of application No. 10/002,818, filed on Nov. 2, 2001, now Pat. No. 6,524,788.

(51) Int. Cl.
*A12Q 1/00* (2006.01)
*G01N 33/53* (2006.01)
*A61K 33/42* (2006.01)
*A61K 33/06* (2006.01)
*A01N 59/26* (2006.01)

(52) U.S. Cl. .................... 435/4; 435/7.1; 436/500; 424/602; 424/682; 514/1; 514/167; 530/350

(58) Field of Classification Search ................ 435/7.1, 435/4; 436/500; 530/300, 350; 424/602, 424/682; 514/1, 167
See application file for complete search history.

(56) References Cited

U.S. PATENT DOCUMENTS

| | | | |
|---|---|---|---|
| 4,369,138 A | 1/1983 | Lindall | 260/112.5 |
| 4,423,037 A | 12/1983 | Rosenblatt et al. | 424/177 |
| 4,508,828 A | 4/1985 | Lindall et al. | 436/500 |
| 4,656,250 A | 4/1987 | Morita et al. | 530/324 |
| 6,030,790 A | 2/2000 | Adermann et al. | 435/7.1 |
| 6,524,788 B1 | 2/2003 | Cantor | |
| 6,689,566 B1 | 2/2004 | Cantor et al. | |
| 6,743,590 B1 | 6/2004 | Cantor et al. | |
| 6,923,968 B1 | 8/2005 | Cantor | |

FOREIGN PATENT DOCUMENTS

| | | |
|---|---|---|
| DE | 33 47 548 | 7/1985 |
| DE | 44 34 551 | 4/1996 |
| EP | 0 783 522 | 12/2001 |
| WO | WO 91/06564 | 5/1991 |
| WO | WO 93/06845 | 4/1993 |
| WO | WO 94/03201 | 2/1994 |
| WO | WO 96/10041 | 4/1996 |

OTHER PUBLICATIONS

Monier-Faugere et al., 2001, Kidney International, vol. 60, pp. 1460-1468.*
Adermann et al., In: *Innovations and Perspectives in Solid Phase Synthesis*, Epton (ed.), Mayflower World Wide, Birmingham (1994) pp. 429-432.
Atkinson et al., Journal of Immunoassay (1982) 3(1):31-51.
Blind et al., Clin. Chem. (1987) 33(8): 1376-1381.
Bowie et al., Science (1990) 247:1306-1310.
Brossard et al., Journal of Clinical Endocrinology and Metabolism (1996) 81(11):3923-3929.
Campbell, Monoclonal Antibody and Immunosensor Technology, in Laboratory Techniques in Biochemistry and Molecular Biology, van der Vliet (ed.), Elsevier (1991) pp. 1-11, 42-45.
Caporale and Rosenblatt, Paraththyroid Hormone Antagonists Effective in vivo, in: Advances in Experimental Medicine and Biology, New York (1986) pp. 315-327.
Clinical Chemistry (1999) 45(6)Suppl:A97 b, Abstract Nos. 339-341.
D'Amour et al., Am. J. Physiol. (1986) 251:E680-E687.
Daniel et al., Virology (1994) 202:540-549.
Divieti, P. et al., *J Bone Miner Res* (2001):Suppl I, S307.
Faugere, M.C. et al., (2001). *Kidney International* 60:1460-1468.
Fischer et al., The Journal of Clinical Investigation (1974) 54:1382-1394.
Gao et al., Clinica Chimica Acta (1996) 245:39-59.
Goodman, W. et al., (2000). *NEJM* 342:20, 1478-1483.
Gordon et al., Parathyroid Hormone Domain for Protein Kinase C Stimulation Located within Amphiphilic Helix, in: Peptides: Chemistry and Biology, Proceedings of the Twelfth American Peptide Symposium, Jun. 16-21, 1991, Cambridge, MA, Smith and River (eds.) Escom Science Publishers (1992) pp. 37-39.
Hashimoto et al., Journal of Cardiovascular Pharmacology (1981) 3(4):668-676.
Hehrmann et al., Journal of Immunoassay (1980) 1(2): 151-174.

(Continued)

Primary Examiner—Olga N. Chernyshev
(74) Attorney, Agent, or Firm—Morrison & Foerster LLP

(57) ABSTRACT

The present invention relates to novel methods for monitoring and guiding therapeutic suppression of parathyroid hormone in renal patients having secondary hyperparathyroidism. One determines and monitors the level of parathyroid hormone agonist and parathyroid hormone antagonist in the renal patient. The parathyroid hormone suppressing therapeutic is administered to the patient so as to minimize the level of parathyroid hormone antagonist.

39 Claims, 2 Drawing Sheets

OTHER PUBLICATIONS

John et al., Journal of Clinical Endocrinology and Metabolism (1999) 84(11):4287-4290.
LePage et al., Clin. Chem. (1998) 44:805-810.
Logue et al., Journal of Immunological Methods (1991) 137:159-166.
Mägerlein et al., Arzneim.-Forsch./Drug Res. (1998) 48(1):197-204.
Mägerlein et al., Arzneim.-Forsch./Drug Res. (1998) 48(11):783-787.
Mallette, Journal of Clinical Endocrinology and Metabolism (1980) 50(1);201-203.
Nakamura et al., Endocrinol. JPN (1981) 28(4):547-549.
Ngo et al., The Protein Folding Problem and Tertiary Structure Prediction, Merz et al., (eds.), Birkhäuser Boston (1994) pp. 492-495.
Niall et al., Proc. Natl. Acad. Sci. USA (1974) 71(2):384-388.
Nussbaum et al., Chemical Abstracts (1982) 96(5):181-192.
Nussbaum, SR et al., Clin. Chem. (1987) 33:1364-67.
Pang et al., Pharmacol. Exp. Ther. (1981) 216(3):567-571.
Qi et al., Am. J. Kidney Dis. (1995) 26:622-631.
Quarles et al., J. Clin. Endocrinol. Metab. (1992) 75:145-150.
Stadler, *Homologous Radioimmunoassay for Human Parathyroid Hormone (Residues 1-34) with Biotinylated Peptide as Tracer, in Calcium Regulating Hormones, Vitamin D Metabolites, and Cyclic AMP Assays and their Clinical Application*, Schmidt-Gayk et al., (eds.), Berlin/Heidelberg, Springer, (1990) pp. 137-150.
Tampe et al., J. Immunoassay (1992) 13(1): 1-13.
Visser et al., Acta Endocrinology (1979) 90:90-102.
Wingender et al., Structure-Function Relationship in Parathyroid Hormone in: Advances in Protein Design, International Workshop, Blöcker et al., (eds.), VCH (1988) pp. 167-176.
Zanelli et at., Journal of Immunoassay (1983) 4(2):175-206.
Zemplar package insert, Abbott Reference (1998) 06-9998-R1-Rev. Roche Laboratories.
U.S. Appl. No. 09/323,606, filed by Tom Cantor on Jan. 1, 1999.
U.S. Appl. No. 09/636,530, filed by Tom Cantor on Aug. 10, 2000.
U.S. Appl. No. 09/636,531, filed by Tom Cantor on Aug. 10, 2000.
U.S. Appl No. 09/928,048, filed by Tom Cantor on Aug. 10, 2001.
U.S. Appl. No. 60/224,396, filed by Tom Cantor on Aug. 10, 2000.
U.S. Appl. No. 10/265,276, filed by Tom Cantor on Oct. 3, 2002.
Faugere et al., Nephrology. Bone & Mineral Metabolism A3995.

\* cited by examiner

Whole Human PTH (1-84)

METHODS FOR MONITORING AND GUIDING THERAPEUTIC SUPPRESSION OF PARATHYROID HORMONE IN RENAL PATIENTS HAVING SECONDARY HYPERPARATHYROIDISM

CROSS-REFERENCE TO RELATED APPLICATIONS

This application is related to U.S. patent application Ser. No. 10/002,818, filed Nov. 2, 2001, now U.S. Pat. No. 6,524,788, which is incorporated herein by reference.

TECHNICAL FIELD

The present invention relates to novel methods for monitoring and guiding therapeutic suppression of parathyroid hormone in renal patients having secondary hyperparathyroidism. One determines and monitors the level of parathyroid hormone agonist and parathyroid hormone antagonist in the renal patient. The parathyroid hormone suppressing therapeutic is administered to the patient so as to minimize the level of parathyroid hormone antagonist.

BACKGROUND ART

Calcium plays an indispensable role in cell permeability, the formation of bones and teeth, blood coagulation, transmission of nerve impulse, and normal muscle contraction. The concentration of calcium ions in the blood is, along with calcitrol and calcitonin, regulated mainly by parathyroid hormone (PTH). Although calcium intake and excretion may vary, PTH serves through a feedback mechanism to maintain a steady concentration of calcium in cells and surrounding fluids. When serum calcium lowers, the parathyroid glands secrete PTH, affecting the release of stored calcium. When serum calcium increases, stored calcium release is retarded through lowered secretions of PTH.

The complete form of human PTH, sometimes referred to in the art as hPTH but referred to in the present invention as an example of PTH agonist, is a unique 84 amino acid peptide (SEQ ID NO:1), as is shown in FIG. 1. Researchers have found that this peptide has an anabolic effect on bone that involves a domain for protein kinase C activation (amino acid residues 28 to 34) as well as a domain for adenylate cyclase activation (amino acid residues 1 to 7). However, various catabolic forms of clipped or fragmented PTH peptides also are found in circulation, most likely formed by intraglandular or peripheral metabolism. For example, whole PTH can be cleaved between amino acids 34 and 35 to produce a (1–34) PTH N-terminal fragment and a (35–84) PTH C-terminal fragment. Likewise, clipping can occur between either amino acids 36 and 37 or 37 and 38. Recently, a large PTH fragment referred to as "non-(1–84) PTH" has been disclosed which is clipped closer to the N-terminal end of PTH. (See R. LePage et al., "*A non-(1–84) circulating parathyroid hormone (PTH) fragment interferes significantly with intact PTH commercial assay measurements in uremic samples,*" Clin. Chem. (1998); 44: 805–810.)

The clinical need for accurate measurement of PTH is well demonstrated. Serum PTH level is one of the most important indices for patients with the following diseases: familial hypocalciuria; hypercalcemia; multiple endocrine neoplasia types I and II; osteoporosis; Paget's bone disease; primary hyperparathyroidism—caused by primary hyperplasia or adenoma of the parathyroid glands; pseudohypoparathyroidism; and renal failure, which can cause secondary hyperparathyroidism.

PTH plays a role in the course of disease in a patient with chronic renal failure. Renal osteodystrophy (RO) is a complex skeletal disease comprising osteitis fibrosa cystica (caused by PTH excess), osteomalacia—unmineralized bone matrix (caused by vitamin D deficiency), extraskeletal calcification/ossification (caused by abnormal calcium and phosphorus metabolism), and adynamic low bone turnover disease (contributed to by PTH suppression). Chronic renal failure patients can develop RO. Failing kidneys increase serum phosphorus hyperphosphoremia) and decrease 1,25-dihydroxyvitamin D (1,25-D) production by the kidney. The former results in secondary hyperparathyroidism from decreased gastrointestinal calcium absorption and osteitis fibrosa cystica from increased PTH in response to an increase in serum phosphorus. The later causes hypocalcemia and osteomalacia. With the onset of secondary hyperparathyroidism, the parathyroid gland becomes less responsive to its hormonal regulators because of decreased expression of its calcium and vitamin D receptors. Serum calcium drops. RO can lead to digital gangrene, bone pain, bone fractures, and muscle weakness.

For chronic renal failure patients with secondary hyperparathyroidism, a number of different therapeutic treatments are available. One can administer calcium carbonate so as to directly adjust the available calcium ion level. However, with the increasing incidence of ectopic calcification, increasing calcium intake is often not desirable. One can administer calcimimetics, such as AMG073 made by Amgen, Inc. of Thousand Oaks, Calif. However, AMG073 has not been approved for use in the USA. One can administer vitamin D analogues, (such as the Calcijex® or Zemplar® brands made by Abbott Labs of Abbott Park, Ill.; Rocaltrol brand made by Roche Laboratories of Basle, Switzerland; Oxarol® brand made by Chugai Pharmaceutical), so as to lower PTH. However, researchers have found that vitamin D analogues can oversuppress PTH, thereby leading to adynamic low bone turnover disease setting the patient at risk of ectopic and vascular calcification. (See the package insert for Zemplar, Abbott Reference 06-9998-R1-Rev, April 1998. See the package insert for Rocaltrol®, Roche Laboratories, inc. November 1998 Product identification Guide, page 334.)

Researchers have also found that a large circulating PTH fragment (e.g., cyclase inactive parathyroid hormone) functions as a naturally occurring PTH antagonist. Cyclase inactive PTH has been found to be useful, alongside whole PTH, as an indicator in separating untreated end stage renal disease (ESRD) patients with high bone turnover from those with adynamic low bone turnover. (See Faugere, M. C. et alia. "*Improved Assessment of Bone Turnover by the PTH 1–84/largeC-PTH fragments ratio in ESRD patients*", Kidney International 2001; 60: 1460–1468.) Moreover, researchers have found that cyclase inactive PTH can cause adynamic low bone turnover by inhibiting the formation of osteoclasts, bone resorption, and bone turnover. (See Divieti, P. et alia, "*In vitro Inhibition of Bone Resorption by Human PTH (7–84)*" J. Bone Miner Res 2001:Suppl 1, S307. See also Faugere, M. C. et alia, "*The Effects of PTH (1–84) on bone turnover are Antagonized by PTH (7–84) in Thyroparathyroidectomized and Nephrectomized Rats*"; J Am Soc Nephrol 12:2001, 764A.)

Determining circulating biologically active PTH levels in humans has been challenging. One major problem is that PTH is found at low levels, normally 10 pg/mL to 65 pg/mL.

Coupled with extremely low circulating levels is the problem of the heterogeneity of PTH and its many circulating fragments. In many cases, immunoassays have faced substantial and significant interference from circulating PTH fragments. For example, some commercially available PTH kits have almost 100% cross-reactivity with the non-(1–84) PTH fragment, (see the LePage article).

PTH immunoassays have varied over the years. One early approach is a double antibody precipitation immunoassay found in U.S. Pat. No. 4,369,138 to Arnold W. Lindall et alia. A first antibody has a high affinity for a (65–84) PTH fragment. A radioactive labeled (65–84) PTH peptide is added to the sample with the first antibody to compete for the endogenous unlabeled peptide. A second antibody is added which binds to any first antibody and radioactive labeled PTH fragment complex, thereby forming a precipitate. Both precipitate and supernatant can be measured for radioactive activity, and endogenous PTH levels can be calculated therefrom.

In an effort to overcome PTH fragment interference, immunoradiometric two-site assays for intact PTH (I-PTH) have been introduced, such as Allegro® Intact PTH assay by the Nichol's Institute of San Juan Capistrano, Calif. In one version, a capture antibody specifically binds to the C-terminal portion of hPTH while a labeled antibody specifically binds to the N-terminal portion of the captured hPTH. In another, two monoclonal antibodies were used, both of which attached to the N-terminal portion of hPTH. Unfortunately, these assays have problems in that they measure but do not discriminate between whole PTH and non-whole PTH peptide fragments. This inability comes to the fore in hyperparathyroid patients and renal failure patients who have significant endogenous concentrations of large, non-whole PTH fragments.

Recently, Scantibodies Laboratory, Inc. of Santee, Calif. USA introduced a series of novel kits that allow for the accurate measurement of both PTH agonist and PTH antagonist. The PTH agonist assay is a direct measurement, while the PTH antagonist assay is a calculated value from the difference of the PTH agonist assay value and a total PTH (including both PTH agonist and PTH antagonist) assay value. A number of unexpected advantages have become available to the physician, including the first non-invasive method for assisting in the differentiation of secondary hyperparathyroid patients with HBT and ALBT.

DISCLOSURE OF THE INVENTION

In one embodiment, a method is provided for monitoring and guiding therapeutic suppression of parathyroid hormone in renal patients having secondary hyperparathyroidism comprising: a) determining and monitoring the level of parathyroid hormone (PTH) agonist in a renal patient having secondary hyperparathyroidism; b) determining and monitoring the level of PTH antagonist in the patient; and c) administering a therapeutic to the patient that suppresses PTH agonist whereby the amount of therapeutic administered is adjusted such that the level of PTH antagonist is minimized. Frequently, the therapeutic is administered in increasing increments from a nominal amount. In addition, frequently steps a) and b) are performed using a sample obtained from a renal patient, which sample may be a serum, plasma and/or blood sample.

In one aspect the renal patient is already receiving the therapeutic, and therapeutic administration is terminated for a time sufficient to allow the patient to return to at least a relatively non-suppressed state. In one aspect, this timing may be measured with respect to parathyroid gland status and/or bone status. Relatedly, the time sufficient to allow the patient to return to at least a relatively non-suppressed state is frequently between about three months to about six months, with respect to bone status. The time sufficient to allow the patient to return to at least a relatively non-suppressed state is frequently between about three minutes to about twenty minutes, with respect to parathyroid gland status. On occasion, the time sufficient to allow the patient to return to at least a relatively non-suppressed state is between about two weeks to about six weeks, or sometimes about four weeks. In addition, while guiding therapy of these patients, the amount of administered therapeutic may be adjusted until the level of PTH antagonist is minimized.

In another aspect of the present invention the therapeutic being administered is selected from the group consisting of calcium, vitamin D, vitamin D analogues, and calcimimetics (e.g., AMG073). Frequently, when vitamin D analogs are used, they may be selected from paricalcitrol, calcitriol, maxacalcitol, alfacalcidol, calcifediol, or ergocalciferol.

In a further aspect of the present invention, the PTH agonist level is compared with the PTH antagonist level. In another aspect, the PTH agonist level is compared with the total parathyroid hormone level. In yet another aspect, the PTH antagonist level is compared with the total parathyroid hormone level. In a further aspect, the PTH agonist level is compared with the PTH antagonist level in the form of a ratio or proportion.

In one aspect, the PTH antagonist level is determined by determining a total PTH level and determining a PTH agonist level followed by subtracting the PTH agonist level from the total PTH level.

In another aspect, the PTH agonist level and the PTH antagonist level are determined using an immunoassay. In yet another aspect, the PTH agonist level is determined using an antibody that distinguishes PTH agonist from PTH antagonist. In a further aspect, frequently the PTH antagonist level is determined using an antibody that distinguishes PTH agonist from PTH antagonist.

In one embodiment, the method above may further comprise monitoring for vascular calcification in the patients. Frequently, vascular calcification is monitored by monitoring alkaline phosphatase levels in the patient.

In another embodiment, the PTH agonist levels and the PTH antagonist levels are compared, individually or together, with corresponding bone biopsy data. In one aspect, the ratio or proportion of PTH agonist to PTH antagonist will be compared with corresponding bone biopsy data. On occasion, bone biopsy data will be used to verify the results of PTH agonist level and/or PTH antagonist level determinations and/or PTH agonist/antagonist ratios. Frequently, the PTH agonist level and the PTH antagonist level determinations are compared with corresponding bone biopsy data after administration of the therapeutic. On occasion, this comparison after administration of the therapeutic is useful to monitor the PTH therapy of patients. Frequently, such treatment is directed to decreasing PTH agonist levels and minimizing PTH antagonist levels.

In a further aspect, the PTH agonist comprises a contiguous portion of human PTH having an amino acid sequence set forth in SEQ ID NO: 1 ($PTH_{1-84}$), and the PTH agonist has the following characteristics: the N-terminal amino acid residue of the PTH agonist starts at position 1 of the $PTH_{1-84}$; and the C-terminal amino acid residue of the PTH agonist ends at any position spanning position 34 through position 84 of the $PTH_{1-84}$. In another aspect, the PTH antagonist comprises a contiguous portion of human PTH having an amino acid sequence set forth in SEQ ID NO: 1 ($PTH_{1-84}$), and the PTH antagonist has the following characteristics: the N-terminal amino acid residue of the PTH antagonist starts at any position spanning position 2 through position 33 of the $PTH_{1-84}$; the C-terminal amino acid residue of the PTH antagonist ends at any position spanning position 35 through position 84 of the $PTH_{1-84}$; and the PTH antagonist has a minimal length of three amino acid residues.

In another embodiment, a method is provided for monitoring and guiding therapeutic suppression of parathyroid hormone in renal patients having secondary hyperparathyroidism comprising: a) obtaining a sample from a renal patient having secondary hyperparathyroidism; b) determining and monitoring the level of PTH antagonist in the renal patient; and c) administering a therapeutic to the patient capable of suppressing a PTH agonist, whereby the amount of therapeutic administered is adjusted such that the level of PTH antagonist is minimized in the patient.

In a further embodiment, kits are provided that are useful for monitoring and guiding therapeutic suppression of parathyroid hormone in renal patients having secondary hyperparathyroidism comprising: a) means for monitoring the level of parathyroid hormone (PTH) agonist in a renal patient having secondary hyperparathyroidism; b) means for monitoring the level of PTH antagonist in the patient; and c) means for administering a therapeutic to the patient that suppresses PTH agonist whereby the amount of therapeutic administered is adjusted such that PTH agonist levels are decreased and the level of PTH antagonist is minimized.

DETAILED DESCRIPTION OF THE INVENTION

Figure 1:
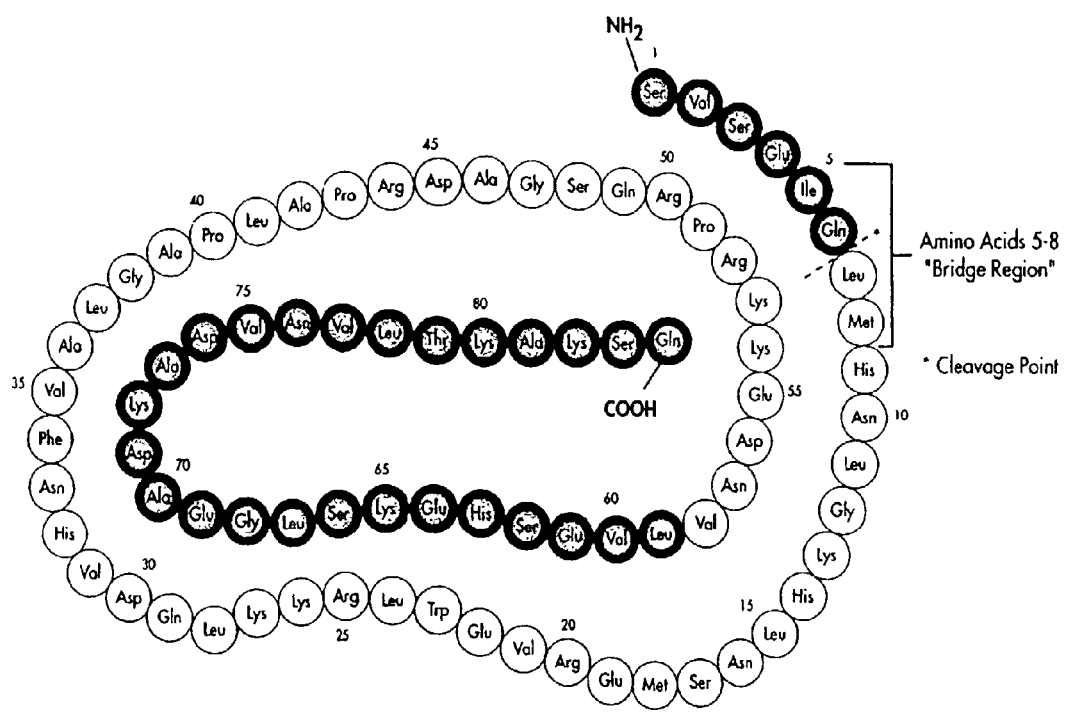
FIG. 1 is a diagrammatic view of human wPTH.

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "parathyroid hormone (PTH) agonist" refers to the complete molecule of PTH or a fragment, derivative or analog thereof that stimulates osteoclasts formation and bone turnover to increase blood calcium levels. PTH agonist further refers to peptides which have PTH agonist properties. Other names of PTH include parathormone and parathyrin. For purposes herein, the name "parathyroid hormone (PTH)" is used herein, although all other names are contemplated. It is intended to encompass PTH agonist with conservative amino acid substitutions that do not substantially alter its biological activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al., MOLECULAR BIOLOGY OF THE GENE, 4th Edition, 1987, The Bejamin/Cummings Pub. Co., p.224). PTH agonist assay values may be obtained by measuring a sample with a Scantibodies Whole PTH Assay or a Scantibodies CAP™ Assay or a $3^{rd}$ generation PTH Assay or a Nichols BioIntact™ PTH assay or an Immutopics™ Human Bioactive PTH assay. "Cyclase activating PTH," "whole PTH," and "CAP" are representative examples of PTH agonists.

As used herein, "parathyroid hormone (PTH) antagonist" refers to a PTH fragment or derivative that counters the effect of a PTH agonist or otherwise lacks PTH agonist activity. It is intended to encompass PTH antagonist with conservative amino acid substitutions that do not substantially alter its activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al. MOLECULAR BIOLOGY OF THE GENE, 4th Edition, 1987, The Bejamin/Cummings Pub. co., p.224). "Cyclase inactive PTH" and "CIP" are representative examples of PTH antagonists.

As used herein, the terms "total PTH," "intact PTH" and "total intact PTH" are interchangeable and refer to an assay directed at measuring PTH agonist and PTH antagonist levels.

As used herein, a "functional derivative or fragment" of PTH agonist or PTH antagonist refers to a derivative or fragment of PTH that still substantially retains its function as a PTH agonist or PTH antagonist. Normally, the derivative or fragment retains at least 50% of its PTH agonist or PTH antagonist activity. Preferably, the derivative or fragment retains at least 60%, 70%, 80%, 90%, 95%, 99% and 100% of its PTH agonist or PTH antagonist activity. It is also possible that a functional derivative or fragment of PTH agonist or PTH antagonist has higher PTH agonist or PTH antagonist activity than a parent molecule from which the functional derivative or fragment is derived from.

As used herein, "treatment" means any manner in which the symptoms of a condition, disorder or disease are ameliorated or otherwise beneficially altered. Treatment also encompasses any pharmaceutical use of the compositions herein.

As used herein, "disease or disorder" refers to a pathological condition in an organism resulting from, e.g., infection or genetic defect, and characterized by identifiable symptoms.

As used herein, "adynamic low bone turnover disease" refers to a variety of disorders involving abnormal PTH agonist and/or antagonist levels in a person. This definition is non-limiting in that it does not refer to only one specific disease, it refers to a variety of disorders that may result from abnormal PTH or PTH component levels in a person. As PTH levels are tied to bone turnover rate, abnormally low levels of PTH agonist, abnormally low levels of PTH agonist/antagonist ratios, and abnormally high levels of PTH antagonist may lead to abnormally low bone turnover in a person. In a person, this type of state may indicate the presence of, or susceptibility to, an adynamic low bone turnover disease. Conversely, abnormally high levels of PTH agonist, abnormally high levels of PTH agonist/antagonist ratios, and abnormally low levels of PTH antagonist may lead to abnormally high bone turnover in a person.

As used herein the term "sample" refers to anything which is suspected of containing an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). Frequently, samples obtained for use in the present invention contain, or are suspected of containing, levels of PTH agonist and/or PTH antagonist that are detectable through methods described and contemplated herein.

As used herein, the term "vitamin D analog" refers to any available source of synthetic vitamin D from a variety of sources for clinical or experimental use. For example, vitamin D analogs may be obtained from sources such as Abbott Laboratories, Bone Care International, Hoffman-La Roche, Ltd., Chugai Pharmaceutical Co., Amgen, Inc., NPS Pharmaceuticals, Inc, Kirin Brewing Company, Ltd., Sumitomo Corp., etc. Examples of vitamin D analogs available from these sources include Calcijex®, Zemplar®, Hectoral®, Rocaltrol®, Oxarol®, etc. In addition, the active ingredients in a variety of synthetic vitamin D sources contemplated herein may include paricalcitrol, calcitriol, maxacalcitol, alfacalcidol, calcifediol, or ergocalciferol.

B. Risk and Therapy Determinations Based on PTH Agonist Levels and PTH Antagonist Levels The present invention relates to novel methods for monitoring and guiding therapeutic suppression of parathyroid hormone in renal patients having secondary hyperparathyroidism. In one aspect, one determines and monitors the level of PTH agonist and PTH antagonist in the renal patient. In another aspect, one determines and monitors the level of PTH agonist in the renal patient. Frequently, the parathyroid hormone suppressing therapeutic is administered to the patient so as to minimize the level of PTH antagonist.

Secondary hyperparathyroidism is a common disease in renal compromised patients, especially those with ESRD. Virtually all ESRD patients have bone disease and mineral metabolism disorders, either high bone turnover disease or adynamic low bone turnover disease. Elevated levels of PTH agonist (with respect to PTH antagonist) lead to high bone turnover disease (HBT). Elevated levels of PTH antagonist (with respect to PTH agonist) lead to adynamic low bone turnover disease (ALBT). In general, the more medically serious of these two disorders is ALBT due to the higher risk of soft tissue calcification that accompanies this disorder. In ALBT ectopic tissue calcification results in vascular stenosis (including occlusion of coronary arteries) and aortic rigidity. Therefore, ALBT patients are subject to a higher likelihood of serious medical complications due to a circulatory system failure, such as myocardial infarction than those with HBT. One reason for this is that it has been difficult in the past to find a reliable therapeutic treatment for ALBT. In addition, the use of therapeutic PTH suppression can lead to therapeutic PTH over-suppression which, in turn, leads to ALBT. In other words, due to the lack of a reliable indicator, PTH agonist suppressant therapy can inadvertently lead to ALBT due to PTH over-suppression.

Difficulty with implementing PTH suppression therapy can be seen in the setting of at least ten different PTH target recommendations within the past decade. The net result of this uncertainty in therapeutic indicators is that the incidence of vascular calcification has been reported to be 88% for ESRD patients. (See Goodman, W. et al., "*Coronary Artery Calcification in Young Adults with End Stage Renal Disease Who Are Undergoing Dialysis*"; NEJM May 18, 2000; 342:20, 1478–1483.)

A novel finding leading to the present invention is that while the PTH agonist level decreases in response to the administration of PTH agonist suppressants, PTH antagonist levels may not. Moreover, oversuppression through the use of PTH agonist suppressants may increase the PTH antagonist level. For an untreated renal patient with an elevated PTH agonist level, the administration of a PTH suppressant will also initially suppress the PTH antagonist level. However, as the PTH suppressant dosage increases, the level of PTH antagonist will reach a minimal level and then start to increase before the level of PTH agonist stops decreasing. To avoid inducing ALBT in such patients, the administration of PTH suppressant should be adjusted so that the PTH antagonist level reaches and stays about the minimal level mentioned above. Ordinarily skilled artisans know that this level may vary from patient to patient, but can determine what is best for a particular patient through monitoring the PTH level response to therapy.

Preferably, PTH agonist levels are measured directly using an assay that does not detect PTH antagonist either in blood, plasma, or serum. For example, Scantibodies Laboratory Whole PTH Assay or Scantibodies Laboratory CAP® Assay are appropriate assays.

PTH antagonist levels should be measured using an assay that either directly detects PTH antagonist (but not PTH agonist) or indirectly through a total PTH measurement that measures the sum of the PTH agonist and PTH antagonist. An indirect measurement subtracts the PTH agonist value from the total PTH value, deriving the PTH antagonist value. Thus, one should use a total PTH assay that is designed to have essentially 100% cross-reactivity with PTH antagonist and PTH agonist. For example, Scantibodies Laboratory Total Intact PTH Assay or Scantibodies Laboratory Intact PTH Assay are appropriate assays.

The present method should be used when a PTH suppressant type therapy is used. Applicable treatments include calcium administration, vitamin D and vitamin D analogue administration, and calcimimetic administration. For untreated ESRD patients, the therapeutic should be administered in increasing increments from an amount nominal for the selected PTH suppressant. If the patient is already receiving PTH suppressant type therapy, one can terminate the therapeutic administration for a time sufficient to allow the patient to return to a relatively non-suppressed state. The time it takes to return to a relatively non-suppressed state may range from about 3 to 5 minutes to about 20 minutes up to about three to about six months.

The relatively non-suppressed state may either account for parathyroid gland status and/or bone status. For example, without being bound by theory, a person may return to a relatively non-suppressed state with respect to the parathyroid gland status in about 3 to about 5 minutes, frequently ranging up to about 20 minutes. This is because the PTH levels in a patient, with respect to parathyroid gland status, my change within minutes of a change in the dose of PTH suppressant, and a return to a relatively non-suppressed state might be considered to occur within minutes. Often times, the return to a relatively non-suppressed state, with respect to the parathyroid gland status, may range from about 10 minutes up to one or more hours or days. Also, for example, without being bound by theory, a person may return to a relatively non-suppressed state with respect to the bone status in about 3 weeks to about 6 months, frequently ranging between about 3 to about 6 months. This range may be 3 months, about 4 months, about 5 months or about 6 months. Often times, the return to a relatively non-suppressed state may range from about 3 or about 4 weeks to about 6 weeks. Also, frequently the time it takes to return to a relatively non-suppressed state may be measured in days or similar increments within the larger range of weeks or months, e.g., between about one to about 6 or about 7 days within a week span.

As an alternative to discontinuing PTH type suppressant therapy, if a patient is already receiving PTH type suppressant therapy, one can adjust the amount of therapeutic, up or down, until the level of PTH antagonist is minimized. Frequently, one would take the PTH agonist level into account while adjusting therapeutic to minimize the level of PTH antagonist. The administering physician can easily determine the appropriate dosage on a patient-by-patient basis. The skilled artisan appreciates that the change in dosage for PTH suppressant may differ from that of another. However, the physician can always be guided by the present procedure to affect the best compromise for each individual patient between PTH over-suppression and abnormally elevated PTH.

C. Parathyroid Hormone Antagonists

In general, a PTH antagonist of the present invention comprises a contiguous portion of human PTH having an amino acid sequence set forth in SEQ ID NO: 1 ($PTH_{1-84}$), or a nucleic acid encoding said portion of human PTH, and said PTH antagonist has the following characteristics: a) the N-terminal amino acid residue of said PTH antagonist starts at any position spanning position 2 through position 33 of said $PTH_{1-84}$; b) the C-terminal amino acid residue of said PTH antagonist ends at any position spanning position 35 through position 84 of said $PTH_{1-84}$; and c) said PTH antagonist has a minimal length of three amino acid residues. Preferably, the PTH antagonist is in the form of a pharmaceutical composition, which pharmaceutical composition comprises an effective amount of the PTH antagonist and a pharmaceutically acceptable carrier or excipient.

The N-terminal amino acid residue of the PTH antagonist can start at any position spanning position 2 through position 33 of said $PTH_{1-84}$. For example, the N-terminal amino acid residue of the PTH antagonist can start at position 2 of the $PTH_{1-84}$. The C-terminal amino acid residue of said PTH antagonist can end at any position spanning position 35 through position 84 of said $PTH_{1-84}$. For example, the C-terminal amino acid residue of the PTH antagonist can end at position 84 of the $PTH_{1-84}$.

In a specific embodiment, the PTH antagonist is a protein or a peptide, or a nucleic acid encoding said protein or peptide, selected from the group consisting of $PTH_{2-84}$ (SEQ ID NO:2), $PTH_{3-84}$ (SEQ ID NO:3), $PTH_{4-84}$ (SEQ ID NO:4), $PTH_{5-84}$ (SEQ ID NO:5), $PTH_{6-84}$ (SEQ ID NO:6), $PTH_{7-84}$ (SEQ ID NO:7), $PTH_{8-84}$ (SEQ ID NO:8), $PTH_{9-84}$ (SEQ ID NO:9), $PTH_{10-84}$ (SEQ ID NO:10), $PTH_{11-84}$ (SEQ ID NO:11), $PTH_{12-84}$ (SEQ ID NO:12), $PTH_{13-84}$ (SEQ ID NO:13), $PTH_{14-84}$ (SEQ ID NO:14), $PTH_{15-84}$ (SEQ ID NO:15), $PTH_{16-84}$ (SEQ ID NO:16), $PTH_{17-84}$ (SEQ ID NO:17), $PTH_{18-84}$ (SEQ ID NO:18), $PTH_{1984}$ (SEQ ID NO:19), $PTH_{20-84}$ (SEQ ID NO:20), $PTH_{21-84}$ (SEQ ID NO:21), $PTH_{22-84}$ (SEQ ID NO:22), $PTH_{23-84}$ (SEQ ID NO:23), $PTH_{24-84}$ (SEQ ID NO:24), $PTH_{25-84}$ (SEQ ID NO:25); $PTH_{2684}$ (SEQ ID NO:26), $PTH_{27-84}$ (SEQ ID NO:27), $PTH_{28-84}$ (SEQ ID NO:28), $PTH_{29-84}$ (SEQ ID NO:29), $PTH_{30-84}$ (SEQ ID NO:30), $PTH_{31-84}$ (SEQ ID NO:3 1), $PTH_{32-84}$ (SEQ ID NO:32), and $PTH_{33-84}$ (SEQ ID NO:33). In another specific embodiment, the PTH antagonist is a protein or a peptide, or a nucleic acid encoding said protein or peptide, selected from the group consisting of $PTH_{7-69}$ (SEQ ID NO:34), $PTH_{7-70}$ (SEQ ID NO:35), $PTH_{7-71}$ (SEQ ID NO:36), $PTH_{7-72}$ (SEQ ID NO:37), $PTH_{7-73}$ (SEQ ID NO:38), $PTH_{7-74}$ (SEQ ID NO:39), $PTH_{7-75}$ (SEQ ID NO:40), $PTH_{7-76}$ (SEQ ID NO:41), $PTH_{7-77}$ (SEQ ID NO:42), $PTH_{7-78}$ (SEQ ID NO:43), $PTH_{7-79}$ (SEQ ID NO:44), $PTH_{7-80}$ (SEQ ID NO:45), $PTH_{7-81}$ (SEQ ID NO:46), $PTH_{7-82}$ (SEQ ID NO:47), $PTH_{7-83}$ (SEQ ID NO:48) and $PTH_{7-84}$ (SEQ ID NO:7).

The PTH antagonist can have any suitable length provided that it maintains its antagonizing activity. For example, the PTH antagonist can have a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82 or 83 amino acid residues.

D. Parathyroid Hormone Agonists

In general, a PTH agonist of the present invention comprises a contiguous portion of human PTH having an amino acid sequence set forth in SEQ ID NO: 1 ($PTH_{1-84}$), and the PTH agonist has the following characteristics: a) the N-terminal amino acid residue of the PTH agonist starts at position 1 of the $PTH_{1-84}$; and b) the C-terminal amino acid residue of the PTH agonist ends at any position spanning position 34 through position 84 of the $PTH_{1-84}$.

Without being bound by theory, the N-terminal amino acid residue of the PTH agonist generally starts at position 1 of said $PTH_{1-84}$. For example, the N-terminal amino acid residue of the PTH agonist can start at position 1 of the $PTH_{1-84}$. The C-terminal amino acid residue of said PTH agonist can end at any position spanning position 34 through position 84 of said $PTH_{1-84}$. For example, the C-terminal amino acid residue of the PTH agonist can end at position 84 of the $PTH_{1-84}$.

The PTH agonist can have any suitable length provided that it maintains its agonizing activity. For example, the PTH agonist can have a length of 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82 or 83 amino acid residues.

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

E. Kits

The invention also provides for kits for carrying out the methods of the invention. Such kits comprise in one or more containers a means for determining and monitoring the level of parathyroid hormone (PTH) agonist in a renal patient having secondary hyperparathyroidism; in one or more containers, a means for determining and monitoring the level of PTH antagonist in the patient alone or in combination with other agents; and a means for administering a therapeutic to the patient that suppresses PTH agonist whereby the amount of therapeutic administered is adjusted such that PTH agonist levels are decreased and the level of PTH antagonist is minimized. Examples of means for determining and monitoring PTH agonist levels in a patient comprise a variety of PTH assays further described herein. And, examples of means for determining and monitoring PTH antagonist levels in a patient comprise a variety of PTH assays further described herein. Preferred forms may be in combination with sterile saline, dextrose solution, or buffered solution, or other pharmaceutically acceptable sterile fluid. Alternatively, useful therapeutic compositions may be lyophilized or dessicated; in this instance, the kit optionally further comprises in a container a pharmaceutically acceptable solution, preferably sterile, to reconstitute the complex to form a solution for injection purposes. Exemplary pharmaceutically acceptable solutions are saline and dextrose solution.

In one aspect, a kit of the invention further comprises a needle or syringe as a means for administering a therapeutic to a patient, preferably packaged in sterile form, for injecting the composition, and/or a packaged alcohol pad. Instructions are optionally included for administration of composition by a physician or by the patient.

Other features and advantages of the invention will be apparent from the following detailed description, and from the claims.

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

EXAMPLES

Example 1

A clinical trial was held for ninety ESRD patients. Each patient had been receiving vitamin D suppressant therapy in accordance with the manufacturer's guidelines. Each patient was removed from the therapy for a washout period of four weeks, and this was confirmed by a rise in PTH measurements after removal of the therapeutic. PTH maxacalcitol (made by Chugai Pharmaceutical Corporation of Tokyo, Japan) suppressant therapy was started after the washout at a constant administration of 5.5 µg intravenously every three days. Blood samples were obtained from each patient after the washout (week 0), six weeks after therapy restart (week 6), and twelve weeks after therapy restart (week 12). The samples were assayed for PTH agonist levels and PTH antagonist levels using the PTH agonist assay and total PTH assay made by Scantibodies Laboratory, Inc. The samples were assayed for bone specific alkaline phosphatase using a commercially available immunoassay from Hybritech, Inc. of San Diego, Calif.

Clinical Results

Figure 2:
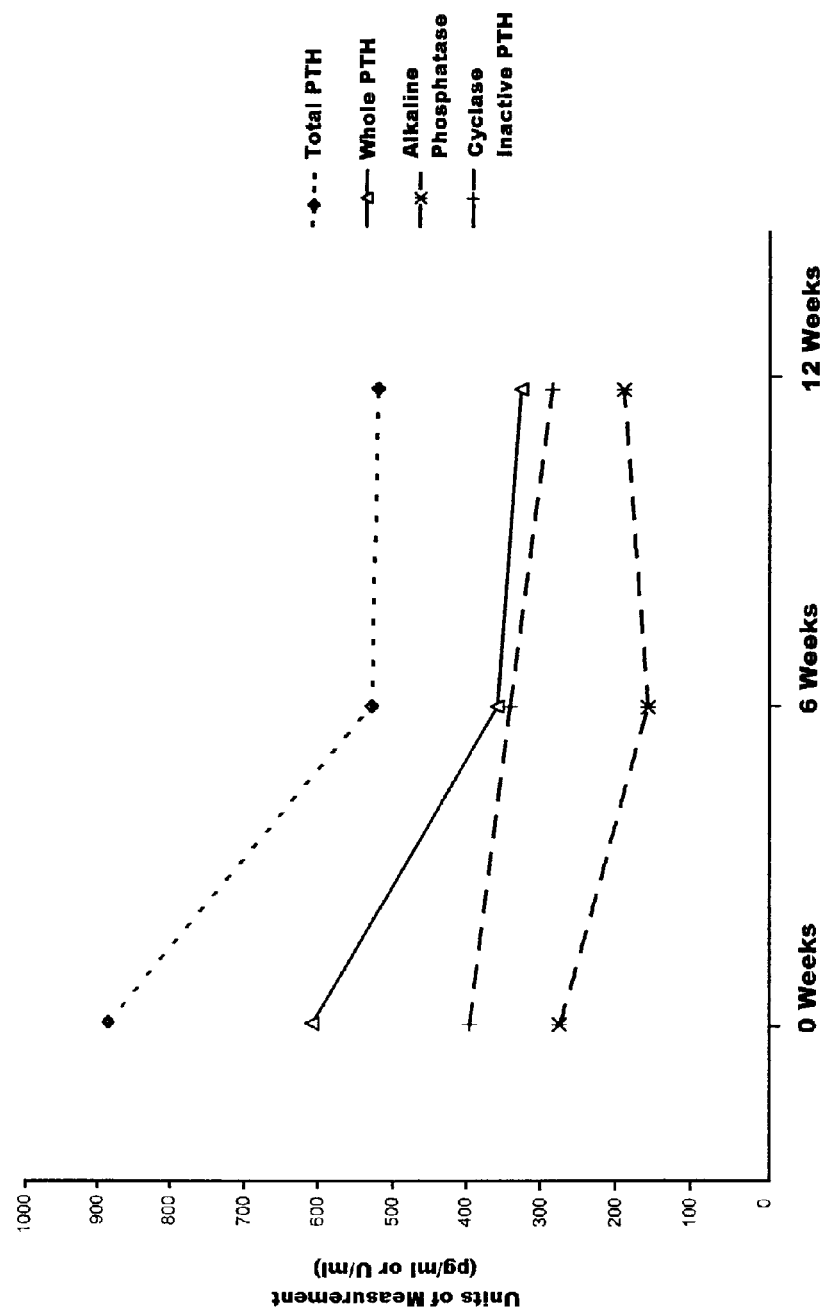
FIG. 2 is a graph comparing PTH measurement parameters over time for patients receiving a PTH suppressant therapy.

The results of the assays for the ninety patients are shown in FIG. 2 and the following table as median values:

TABLE

| Parameter | Time 0 Weeks | Time 6 weeks | Time 12 weeks |
|---|---|---|---|
| Total PTH pg/ml | 886 | 531 (41% decrease) | 525 (1% decrease) |
| PTH agonist pg/ml | 609 | 361 (41% decrease) | 331 (8% decrease) |
| PTH antagonist pg/ml | 276 | 160 (42% decrease) | 194 (21% increase) |
| Alkaline Phosphatase U/ml | 396 | 344 (13% decrease) | 290 (16% decrease) |

The Table shows how the PTH suppressant lowered both the PTH agonist and the total PTH values. After six weeks, the PTH agonist and the total PTH values have decreased by 41%. However, after twelve weeks, these values have decreased a mere 8% (PTH agonist) and 0.8% (total PTH). These results indicate that the PTH suppressant is having difficulty driving the PTH agonist levels down any further. Moreover, the levels of total PTH and PTH agonist are still commonly regarded as being above normal levels (of less than 37 pg/ml for PTH agonist and less than 65 pg/ml for total PTH, see, e.g., Nussbaum SR, et al., "*Highly sensitive two-site immunoradiometric assay of parathyrin, and its clinical utility in evaluating patients with hypercalcemia,*" Clin. Chem. 1987; 33:1364–67) for non-ESRD patients.

The Table provided above indicates the difference in response of PTH antagonist to the PTH suppressant versus the total PTH and PTH agonist response. After six weeks, the PTH antagonist level has decreased by 42%, consistent with the PTH agonist levels after six weeks. However, after twelve weeks, the PTH antagonist level increases by 21%, in contrast to PTH agonist levels. The continued use of PTH suppressant at this level will elevate the PTH antagonist levels. Over a period of time, the increase in PTH antagonist levels will lead to ALBT and subsequent vascular calcification (as confirmed in the Table by the further drop in alkaline phosphatase at twelve weeks). These patients need to have the PTH suppressant dosage lowered to maintain the PTH antagonist at a minimal (in this case 160 pg/ml) level. The medical benefit realized in reducing the PTH agonist level beyond a particular level, even by a small percentage, is far outweighed by the harm caused by the resulting elevation of the PTH antagonist level. This rise in the PTH antagonist level may cause ALBT by inhibiting osteoclast formation, a necessary component in healthy bone modeling involving bone resorption and bone turnover.

Example 2

To verify that PTH agonist and PTH antagonist concentrations and the PTH agonist/antagonist ratio accurately discriminate between high and low bone turnover in renal patients, bone biopsy data is obtained from renal patients having secondary hyperparathyroidism. See Faugere, M-C, et. al., Kidney Int'l. 2001; 60:1460–68. Bone biopsy data will also verify that calculation and evaluation of both PTH agonist and PTH antagonist level data in renal patients provides a more useful therapeutic and prognostic indicator than evaluation of PTH agonist data alone.

Experimental Design

Patients with a total PTH greater than 200 pg/ml (as measured by an Intact PTH assay), will have PTH agonist and PTH antagonist levels and the PTH agonist/antagonist ratio determined by Scantibodies® CAP™ PTH assay (PTH agonist), Scantibodies® Whole PTH assay (PTH agonist), Scantibodies® total intact PTH assay (total PTH) and/or Scantibodies® intact PTH assay (total PTH). Those with a total PTH level greater than 400 pg/ml, or between 200–400 pg/ml, and a PTH agonist/antagonist ratio less than 1.5 will undergo double tetracycline bone labeling and outpatient percutaneous needle biopsy of the pelvic crest bone, under local anesthesia.

These patients will also have their bone specific alkaline phosphatase and TRAP (tartrate resistant acid phosphatase) measured through known means. In addition, x-ray data will be obtained from each patient through the use of mamographic x-ray techniques known in the art.

Patient Population & Selection Criteria

A large cross-section of hemodialysis and peritoneal dialysis patients will be evaluated in this study. All dialysis patients will be included in the initial patient population selection. However, exclusion criteria includes patients that are generally considered too ill to participate in the study, those whose anticoagulation cannot be discontinued for about 48 to 72 hours, and those that are unable to cooperate with study requirements. At least 30 to 50 percent of the dialysis population is likely to have PTH values in the range required to be considered for bone biopsy.

Results

Bone biopsy results are correlated with results of the PTH level assays to verify the accuracy of the PTH agonist/antagonist ratio, versus the PTH agonist measurement alone, in determining a patient's bone turnover rate. Biochemical and radiological data are used to verify these results. As known clinical co-morbidities and therapies have an effect on bone turnover, the effects of these are taken into account in evaluating the data.

The bone biopsy data confirm the efficacy of the PTH agonist/antagonist level comparison and therapy is guided based on a comparison of PTH agonist levels with PTH antagonist levels. Therapy is provided to reduce PTH agonist levels and to minimize PTH antagonist levels in the patients.

After twelve months, biochemical and radiological parameters are reanalyzed, and repeat bone biopsies are performed in order to assess the clinical benefit of the PTH agonist/antagonist ratio analysis approach.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

Citation of the above publications or documents is not intended as an admission that any of the foregoing is pertinent prior art, nor does it constitute any admission as to the contents or date of these publications or documents.

I claim:

1. A method for monitoring and guiding therapeutic suppression of parathyroid hormone in a renal patient having secondary hyperparathyroidism, said method comprising:
   a) obtaining a sample of blood, serum or plasma from said renal patient;
   b) determining and monitoring the level of a parathyroid hormone (PTH) agonist in said sample,
      wherein said agonist comprises a contiguous segment of human PTH having the amino acid sequence SEQ ID NO:1,
      wherein said segment starts at position 1 of human PTH, and ends at any position from position 34 through position 84 of human PTH;
   c) determining and monitoring the level of a PTH antagonist in said sample,
      wherein said antagonist comprises a contiguous portion of human PTH having the amino acid sequence SEQ ID NO:1,
      wherein said portion starts at any position from position 2 through position 33 of human PTH, ends at any position from position 35 through position 84 of human PTH, and has a minimal length of three amino acid residues; and
   d) administering a therapeutic that suppresses PTH agonist to the patient whereby the amount of therapeutic administered is adjusted such that PTH agonist levels are decreased and the level of PTH antagonist is minimized.

2. The method of claim 1, wherein the therapeutic is administered in increasing increments from a nominal amount.

3. The method of claim 1, wherein the patient is already receiving the therapeutic, also comprising adjusting the amount of therapeutic until the level of PTH antagonist is minimized.

4. The method of claim 1, wherein the therapeutic is selected from the group consisting of vitamin D or vitamin D analogue treatment, calcium treatment, or calcimimetic administration.

5. The method of claim 4, wherein the vitamin D analogue comprises paricalcitrol, calcitriol, maxacalcitol, alfacalcidol, calcifediol, or ergocalciferol.

6. The method of claim 1, wherein the PTH agonist level is further compared with the PTH antagonist level.

7. The method of claim 1, wherein the PTH antagonist level is determined by determining the patient's total parathyroid hormone level and subtracting the PTH agonist level from the total parathyroid hormone level.

8. The method of claim 1, wherein the patient's total parathyroid hormone level is determined, and the PTH agonist level is further compared with the total parathyroid hormone level.

9. The method of claim 1, wherein the patient's total parathyroid hormone level is determined, and the PTH antagonist level is further compared with the total parathyroid hormone level.

10. The method of claim 1, wherein the PTH agonist level is further compared with the PTH antagonist level in the form of a ratio or proportion.

11. The method of claim 1, wherein the hyperparathyroidism is caused by chronic renal failure.

12. The method of claim 1, wherein the PTH agonist level and the PTH antagonist level are determined using an immunoassay.

13. The method of claim 12, wherein the PTH agonist level is determined using an antibody that distinguishes PTH agonist from PTH antagonist.

14. The method of claim 12, wherein the PTH antagonist level is determined using an antibody that distinguishes PTH agonist from PTH antagonist.

15. The method of claim 1, further comprising monitoring for vascular calcification in the patients.

16. The method of claim 15, wherein the vascular calcification is monitored by monitoring alkaline phosphatase level.

17. The method of claim 1, wherein the patient is already receiving the therapeutic, also comprising terminating the therapeutic administration for a time sufficient to allow the patient to return to at least a relatively non-suppressed state.

18. The method of claim 17, wherein the time sufficient to allow the patient to return to at least a relatively non-suppressed state is between about three months to about six months.

19. The method of claim 17, wherein the time sufficient to allow the patient to return to at least a relatively non-suppressed state is about three minutes to about twenty minutes.

20. The method of claim 1, wherein the PTH agonist is a peptide having an amino acid sequence of human $PTH_{1-84}$ set forth in SEQ ID NO:1.

21. The method of claim 1, wherein the PTH antagonist is a peptide having an amino acid sequence of human PTH7–84 (SEQ ID NO: 7).

22. The method of claim 1, wherein the PTH agonist level and the PTH antagonist level determinations are further compared with bone biopsy data.

23. The method of claim 22, wherein, after administration of the therapeutic, the PTH agonist level and the PTH antagonist level determinations are compared with bone biopsy data.

24. The method of claim 10, wherein the ratio or proportion determination is further compared with bone biopsy data.

25. A method for monitoring and guiding therapeutic suppression of parathyroid hormone having the sequence set forth in SEQ ID NO:1 in a renal patient having secondary hyperparathyroidism, said method comprising:
   a) obtaining a sample of blood, serum or plasma from the patient;
   b) determining and monitoring the level of a parathyroid hormone (PTH) antagonist in the sample,
   wherein said antagonist comprises a contiguous portion of human PTH having the amino acid sequence SEQ ID NO:1,
   wherein said portion starts at any position from position 2 through position 33 of human PTH, ends at any position from position 35 through position 84 of human PTH, and has a minimal length of three amino acid residues; and
   c) administering to the patient a therapeutic capable of suppressing a PTH agonist, whereby the amount of therapeutic administered is adjusted such that the level of PTH antagonist is minimized in the patient.

26. The method of claim 25, wherein the therapeutic is administered in increasing increments from a nominal amount.

27. The method of claim 25, wherein the therapeutic is selected from the group consisting of vitamin D, a vitamin D analogue, calcium, or a calcimimetic.

28. The method of claim 27, wherein the vitamin D analogue comprises paricalcitrol, calcitriol, maxacalcitol, alfacalcidol, calcifediol, or ergocalciferol.

29. The method of claim 25, further comprising monitoring for vascular calcification in said patients.

30. The method of claim 29, wherein vascular calcification is monitored by monitoring alkaline phosphatase levels.

31. The method of claim 25, wherein the patient is already receiving the therapeutic, also comprising terminating the therapeutic administration for a time sufficient to allow the patient to return to at least a relatively non-suppressed state.

32. The method of claim 31, wherein the time sufficient to allow the patient to return to at least a relatively non-suppressed state is between about three months to about six months.

33. The method of claim 31, wherein the time sufficient to allow the patient to return to at least a relatively non-suppressed state is about three minutes to about twenty minutes.

34. The method of claim 25, wherein the PTH antagonist level is determined by determining the total PTH level and the PTH agonist level, and subtracting the PTH agonist level from the total PTH level, wherein the PTH antagonist level is then compared with the PTH agonist level.

35. A method for determining an appropriate dosage of a therapeutic for suppression of parathyroid hormone having the sequence set forth in SEQ ID NO:1 in a renal patient having secondary hyperparathyroidism, said method comprising:
   a) administering a therapeutic capable of suppressing PTH to said renal patient;
   b) obtaining a sample of blood, plasma or serum from said renal patient;
   c) determining the level of a PTH antagonist in the sample,
   wherein said antagonist comprises a contiguous portion of human PTH having the amino acid sequence SEQ ID NO:1,
   wherein said portion starts at any position from position 2 through position 33 of human PTH, ends at any position from position 35 through position 84 of human PTH, and has a minimal length of three amino acid residues; and
   d) adjusting the dosage of said therapeutic up or down;
   e) monitoring the level of said PTH antagonist in said patient by obtaining an additional sample of blood, plasma, or serum from the patient and measuring the level of said PTH antagonist in said sample; and f) further adjusting the dosage of said therapeutic up or down until the level of said PTH antagonist is minimized.

36. The method of claim 35, wherein said PTH antagonist comprises PTH$_{7-84}$ as set forth in SEQ ID NO: 7.

37. The method of claim 35, further comprising monitoring the level of a PTH agonist in said patient, wherein said agonist comprises a contiguous segment of human PTH having the amino acid sequence SEQ ID NO:1, wherein said segment starts at position 1 of human PTH, and ends at any position from position 34 through position 84 of human PTH.

38. The method of claim 36, wherein said PTH agonist comprises PTH1–84 as set forth in SEQ ID NO:1.

39. The method of claim 38, whereby the amount of therapeutic administered is adjusted to lower the measured levels of PTH antagonist and PTH agonist in the patient.

* * * * *

SEQUENCE LISTING

```
<160> NUMBER OF SEQ ID NOS: 48

<210> SEQ ID NO 1
<211> LENGTH: 84
<212> TYPE: PRT
<213> ORGANISM: Homo sapiens
<220> FEATURE:
<221> NAME/KEY: PEPTIDE
<222> LOCATION: (1)...(84)
<223> OTHER INFORMATION: human parathyroid hormone peptide fragment

<400> SEQUENCE: 1

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 2
<211> LENGTH: 83
<212> TYPE: PRT
<213> ORGANISM: Homo sapiens
<220> FEATURE:
<221> NAME/KEY: PEPTIDE
```

```
<222> LOCATION: (1)...(83)
<223> OTHER INFORMATION: human parathyroid hormone peptide fragment

<400> SEQUENCE: 2

Val Ser Glu Ile Gln Leu Met His Asn Leu Gly Lys His Leu Asn Ser
 1               5                  10                  15

Met Glu Arg Val Glu Trp Leu Arg Lys Lys Leu Gln Asp Val His Asn
            20                  25                  30

Phe Val Ala Leu Gly Ala Pro Leu Ala Pro Arg Asp Ala Gly Ser Gln
        35                  40                  45

Arg Pro Arg Lys Lys Glu Asp Asn Val Leu Val Glu Ser His Glu Lys
    50                  55                  60

Ser Leu Gly Glu Ala Asp Lys Ala Asp Val Asn Val Leu Thr Lys Ala
65                  70                  75                  80

Lys Ser Gln

<210> SEQ ID NO 3
<211> LENGTH: 82
<212> TYPE: PRT
<213> ORGANISM: Homo sapiens
<220> FEATURE:
<221> NAME/KEY: PEPTIDE
<222> LOCATION: (1)...(82)
<223> OTHER INFORMATION: human parathyroid hormone peptide fragment

<400> SEQUENCE: 3

Ser Glu Ile Gln Leu Met His Asn Leu Gly Lys His Leu Asn Ser Met
 1               5                  10                  15

Glu Arg Val Glu Trp Leu Arg Lys Lys Leu Gln Asp Val His Asn Phe
            20                  25                  30

Val Ala Leu Gly Ala Pro Leu Ala Pro Arg Asp Ala Gly Ser Gln Arg
        35                  40                  45

Pro Arg Lys Lys Glu Asp Asn Val Leu Val Glu Ser His Glu Lys Ser
    50                  55                  60

Leu Gly Glu Ala Asp Lys Ala Asp Val Asn Val Leu Thr Lys Ala Lys
65                  70                  75                  80

Ser Gln

<210> SEQ ID NO 4
<211> LENGTH: 81
<212> TYPE: PRT
<213> ORGANISM: Homo sapiens
<220> FEATURE:
<221> NAME/KEY: PEPTIDE
<222> LOCATION: (1)...(81)
<223> OTHER INFORMATION: human parathyroid hormone peptide fragment

<400> SEQUENCE: 4

Glu Ile Gln Leu Met His Asn Leu Gly Lys His Leu Asn Ser Met Glu
 1               5                  10                  15

Arg Val Glu Trp Leu Arg Lys Lys Leu Gln Asp Val His Asn Phe Val
            20                  25                  30

Ala Leu Gly Ala Pro Leu Ala Pro Arg Asp Ala Gly Ser Gln Arg Pro
        35                  40                  45

Arg Lys Lys Glu Asp Asn Val Leu Val Glu Ser His Glu Lys Ser Leu
    50                  55                  60

Gly Glu Ala Asp Lys Ala Asp Val Asn Val Leu Thr Lys Ala Lys Ser
65                  70                  75                  80

Gln
```

-continued

```
<210> SEQ ID NO 5
<211> LENGTH: 80
<212> TYPE: PRT
<213> ORGANISM: Homo sapiens
<220> FEATURE:
<221> NAME/KEY: PEPTIDE
<222> LOCATION: (1)...(80)
<223> OTHER INFORMATION: human parathyroid hormone peptide fragment

<400> SEQUENCE: 5

Ile Gln Leu Met His Asn Leu Gly Lys His Leu Asn Ser Met Glu Arg
 1               5                  10                  15

Val Glu Trp Leu Arg Lys Lys Leu Gln Asp Val His Asn Phe Val Ala
                20                  25                  30

Leu Gly Ala Pro Leu Ala Pro Arg Asp Ala Gly Ser Gln Arg Pro Arg
            35                  40                  45

Lys Lys Glu Asp Asn Val Leu Val Glu Ser His Glu Lys Ser Leu Gly
 50                  55                  60

Glu Ala Asp Lys Ala Asp Val Asn Val Leu Thr Lys Ala Lys Ser Gln
 65                  70                  75                  80

<210> SEQ ID NO 6
<211> LENGTH: 79
<212> TYPE: PRT
<213> ORGANISM: Homo sapiens
<220> FEATURE:
<221> NAME/KEY: PEPTIDE
<222> LOCATION: (1)...(79)
<223> OTHER INFORMATION: human parathyroid hormone peptide fragment

<400> SEQUENCE: 6

Gln Leu Met His Asn Leu Gly Lys His Leu Asn Ser Met Glu Arg Val
 1               5                  10                  15

Glu Trp Leu Arg Lys Lys Leu Gln Asp Val His Asn Phe Val Ala Leu
                20                  25                  30

Gly Ala Pro Leu Ala Pro Arg Asp Ala Gly Ser Gln Arg Pro Arg Lys
            35                  40                  45

Lys Glu Asp Asn Val Leu Val Glu Ser His Glu Lys Ser Leu Gly Glu
 50                  55                  60

Ala Asp Lys Ala Asp Val Asn Val Leu Thr Lys Ala Lys Ser Gln
 65                  70                  75

<210> SEQ ID NO 7
<211> LENGTH: 78
<212> TYPE: PRT
<213> ORGANISM: Homo sapiens
<220> FEATURE:
<221> NAME/KEY: PEPTIDE
<222> LOCATION: (1)...(78)
<223> OTHER INFORMATION: human parathyroid hormone peptide fragment

<400> SEQUENCE: 7

Leu Met His Asn Leu Gly Lys His Leu Asn Ser Met Glu Arg Val Glu
 1               5                  10                  15

Trp Leu Arg Lys Lys Leu Gln Asp Val His Asn Phe Val Ala Leu Gly
                20                  25                  30

Ala Pro Leu Ala Pro Arg Asp Ala Gly Ser Gln Arg Pro Arg Lys Lys
            35                  40                  45

Glu Asp Asn Val Leu Val Glu Ser His Glu Lys Ser Leu Gly Glu Ala
 50                  55                  60
```

```
Asp Lys Ala Asp Val Asn Val Leu Thr Lys Ala Lys Ser Gln
 65                  70                  75
```

<210> SEQ ID NO 8
<211> LENGTH: 77
<212> TYPE: PRT
<213> ORGANISM: Homo sapiens
<220> FEATURE:
<221> NAME/KEY: PEPTIDE
<222> LOCATION: (1)...(77)
<223> OTHER INFORMATION: human parathyroid hormone peptide fragment

<400> SEQUENCE: 8

```
Met His Asn Leu Gly Lys His Leu Asn Ser Met Glu Arg Val Glu Trp
  1               5                  10                  15

Leu Arg Lys Lys Leu Gln Asp Val His Asn Phe Val Ala Leu Gly Ala
                 20                  25                  30

Pro Leu Ala Pro Arg Asp Ala Gly Ser Gln Arg Pro Arg Lys Lys Glu
             35                  40                  45

Asp Asn Val Leu Val Glu Ser His Glu Lys Ser Leu Gly Glu Ala Asp
         50                  55                  60

Lys Ala Asp Val Asn Val Leu Thr Lys Ala Lys Ser Gln
 65                  70                  75
```

<210> SEQ ID NO 9
<211> LENGTH: 76
<212> TYPE: PRT
<213> ORGANISM: Homo sapiens
<220> FEATURE:
<221> NAME/KEY: PEPTIDE
<222> LOCATION: (1)...(76)
<223> OTHER INFORMATION: human parathyroid hormone peptide fragment

<400> SEQUENCE: 9

```
His Asn Leu Gly Lys His Leu Asn Ser Met Glu Arg Val Glu Trp Leu
  1               5                  10                  15

Arg Lys Lys Leu Gln Asp Val His Asn Phe Val Ala Leu Gly Ala Pro
                 20                  25                  30

Leu Ala Pro Arg Asp Ala Gly Ser Gln Arg Pro Arg Lys Lys Glu Asp
             35                  40                  45

Asn Val Leu Val Glu Ser His Glu Lys Ser Leu Gly Glu Ala Asp Lys
         50                  55                  60

Ala Asp Val Asn Val Leu Thr Lys Ala Lys Ser Gln
 65                  70                  75
```

<210> SEQ ID NO 10
<211> LENGTH: 75
<212> TYPE: PRT
<213> ORGANISM: Homo sapiens
<220> FEATURE:
<221> NAME/KEY: PEPTIDE
<222> LOCATION: (1)...(75)
<223> OTHER INFORMATION: human parathyroid hormone peptide fragment

<400> SEQUENCE: 10

```
Asn Leu Gly Lys His Leu Asn Ser Met Glu Arg Val Glu Trp Leu Arg
  1               5                  10                  15

Lys Lys Leu Gln Asp Val His Asn Phe Val Ala Leu Gly Ala Pro Leu
                 20                  25                  30

Ala Pro Arg Asp Ala Gly Ser Gln Arg Pro Arg Lys Lys Glu Asp Asn
             35                  40                  45
```

```
Val Leu Val Glu Ser His Glu Lys Ser Leu Gly Glu Ala Asp Lys Ala
 50                  55                  60

Asp Val Asn Val Leu Thr Lys Ala Lys Ser Gln
 65                  70                  75
```

<210> SEQ ID NO 11
<211> LENGTH: 74
<212> TYPE: PRT
<213> ORGANISM: Homo sapiens
<220> FEATURE:
<221> NAME/KEY: PEPTIDE
<222> LOCATION: (1)...(74)
<223> OTHER INFORMATION: human parathyroid hormone peptide fragment

<400> SEQUENCE: 11

```
Leu Gly Lys His Leu Asn Ser Met Glu Arg Val Glu Trp Leu Arg Lys
  1               5                  10                  15

Lys Leu Gln Asp Val His Asn Phe Val Ala Leu Gly Ala Pro Leu Ala
                 20                  25                  30

Pro Arg Asp Ala Gly Ser Gln Arg Pro Arg Lys Lys Glu Asp Asn Val
             35                  40                  45

Leu Val Glu Ser His Glu Lys Ser Leu Gly Glu Ala Asp Lys Ala Asp
 50                  55                  60

Val Asn Val Leu Thr Lys Ala Lys Ser Gln
 65                  70
```

<210> SEQ ID NO 12
<211> LENGTH: 73
<212> TYPE: PRT
<213> ORGANISM: Homo sapiens
<220> FEATURE:
<221> NAME/KEY: PEPTIDE
<222> LOCATION: (1)...(73)
<223> OTHER INFORMATION: human parathyroid hormone peptide fragment

<400> SEQUENCE: 12

```
Gly Lys His Leu Asn Ser Met Glu Arg Val Glu Trp Leu Arg Lys Lys
  1               5                  10                  15

Leu Gln Asp Val His Asn Phe Val Ala Leu Gly Ala Pro Leu Ala Pro
                 20                  25                  30

Arg Asp Ala Gly Ser Gln Arg Pro Arg Lys Lys Glu Asp Asn Val Leu
             35                  40                  45

Val Glu Ser His Glu Lys Ser Leu Gly Glu Ala Asp Lys Ala Asp Val
 50                  55                  60

Asn Val Leu Thr Lys Ala Lys Ser Gln
 65                  70
```

<210> SEQ ID NO 13
<211> LENGTH: 72
<212> TYPE: PRT
<213> ORGANISM: Homo sapiens
<220> FEATURE:
<221> NAME/KEY: PEPTIDE
<222> LOCATION: (1)...(72)
<223> OTHER INFORMATION: human parathyroid hormone peptide fragment

<400> SEQUENCE: 13

```
Lys His Leu Asn Ser Met Glu Arg Val Glu Trp Leu Arg Lys Lys Leu
  1               5                  10                  15

Gln Asp Val His Asn Phe Val Ala Leu Gly Ala Pro Leu Ala Pro Arg
                 20                  25                  30
```

```
Asp Ala Gly Ser Gln Arg Pro Arg Lys Lys Glu Asp Asn Val Leu Val
        35                  40                  45

Glu Ser His Glu Lys Ser Leu Gly Glu Ala Asp Lys Ala Asp Val Asn
 50                  55                  60

Val Leu Thr Lys Ala Lys Ser Gln
 65                  70
```

<210> SEQ ID NO 14
<211> LENGTH: 71
<212> TYPE: PRT
<213> ORGANISM: Homo sapiens
<220> FEATURE:
<221> NAME/KEY: PEPTIDE
<222> LOCATION: (1)...(71)
<223> OTHER INFORMATION: human parathyroid hormone peptide fragment

<400> SEQUENCE: 14

```
His Leu Asn Ser Met Glu Arg Val Glu Trp Leu Arg Lys Lys Leu Gln
 1               5                  10                  15

Asp Val His Asn Phe Val Ala Leu Gly Ala Pro Leu Ala Pro Arg Asp
                20                  25                  30

Ala Gly Ser Gln Arg Pro Arg Lys Lys Glu Asp Asn Val Leu Val Glu
            35                  40                  45

Ser His Glu Lys Ser Leu Gly Glu Ala Asp Lys Ala Asp Val Asn Val
        50                  55                  60

Leu Thr Lys Ala Lys Ser Gln
 65                  70
```

<210> SEQ ID NO 15
<211> LENGTH: 70
<212> TYPE: PRT
<213> ORGANISM: Homo sapiens
<220> FEATURE:
<221> NAME/KEY: PEPTIDE
<222> LOCATION: (1)...(70)
<223> OTHER INFORMATION: human parathyroid hormone peptide fragment

<400> SEQUENCE: 15

```
Leu Asn Ser Met Glu Arg Val Glu Trp Leu Arg Lys Lys Leu Gln Asp
 1               5                  10                  15

Val His Asn Phe Val Ala Leu Gly Ala Pro Leu Ala Pro Arg Asp Ala
                20                  25                  30

Gly Ser Gln Arg Pro Arg Lys Lys Glu Asp Asn Val Leu Val Glu Ser
            35                  40                  45

His Glu Lys Ser Leu Gly Glu Ala Asp Lys Ala Asp Val Asn Val Leu
        50                  55                  60

Thr Lys Ala Lys Ser Gln
 65                  70
```

<210> SEQ ID NO 16
<211> LENGTH: 69
<212> TYPE: PRT
<213> ORGANISM: Homo sapiens
<220> FEATURE:
<221> NAME/KEY: PEPTIDE
<222> LOCATION: (1)...(69)
<223> OTHER INFORMATION: human parathyroid hormone peptide fragment

<400> SEQUENCE: 16

```
Asn Ser Met Glu Arg Val Glu Trp Leu Arg Lys Lys Leu Gln Asp Val
 1               5                  10                  15
```

```
His Asn Phe Val Ala Leu Gly Ala Pro Leu Ala Pro Arg Asp Ala Gly
            20                  25                  30

Ser Gln Arg Pro Arg Lys Lys Glu Asp Asn Val Leu Val Glu Ser His
        35                  40                  45

Glu Lys Ser Leu Gly Glu Ala Asp Lys Ala Asp Val Asn Val Leu Thr
    50                  55                  60

Lys Ala Lys Ser Gln
65
```

```
<210> SEQ ID NO 17
<211> LENGTH: 68
<212> TYPE: PRT
<213> ORGANISM: Homo sapiens
<220> FEATURE:
<221> NAME/KEY: PEPTIDE
<222> LOCATION: (1)...(68)
<223> OTHER INFORMATION: human parathyroid hormone peptide fragment

<400> SEQUENCE: 17

Ser Met Glu Arg Val Glu Trp Leu Arg Lys Lys Leu Gln Asp Val His
 1               5                  10                  15

Asn Phe Val Ala Leu Gly Ala Pro Leu Ala Pro Arg Asp Ala Gly Ser
            20                  25                  30

Gln Arg Pro Arg Lys Lys Glu Asp Asn Val Leu Val Glu Ser His Glu
        35                  40                  45

Lys Ser Leu Gly Glu Ala Asp Lys Ala Asp Val Asn Val Leu Thr Lys
    50                  55                  60

Ala Lys Ser Gln
65
```

```
<210> SEQ ID NO 18
<211> LENGTH: 67
<212> TYPE: PRT
<213> ORGANISM: Homo sapiens
<220> FEATURE:
<221> NAME/KEY: PEPTIDE
<222> LOCATION: (1)...(67)
<223> OTHER INFORMATION: human parathyroid hormone peptide fragment

<400> SEQUENCE: 18

Met Glu Arg Val Glu Trp Leu Arg Lys Lys Leu Gln Asp Val His Asn
 1               5                  10                  15

Phe Val Ala Leu Gly Ala Pro Leu Ala Pro Arg Asp Ala Gly Ser Gln
            20                  25                  30

Arg Pro Arg Lys Lys Glu Asp Asn Val Leu Val Glu Ser His Glu Lys
        35                  40                  45

Ser Leu Gly Glu Ala Asp Lys Ala Asp Val Asn Val Leu Thr Lys Ala
    50                  55                  60

Lys Ser Gln
65
```

```
<210> SEQ ID NO 19
<211> LENGTH: 66
<212> TYPE: PRT
<213> ORGANISM: Homo sapiens
<220> FEATURE:
<221> NAME/KEY: PEPTIDE
<222> LOCATION: (1)...(66)
<223> OTHER INFORMATION: human parathyroid hormone peptide fragment

<400> SEQUENCE: 19
```

```
Glu Arg Val Glu Trp Leu Arg Lys Lys Leu Gln Asp Val His Asn Phe
 1               5                  10                  15

Val Ala Leu Gly Ala Pro Leu Ala Pro Arg Asp Ala Gly Ser Gln Arg
             20                  25                  30

Pro Arg Lys Lys Glu Asp Asn Val Leu Val Glu Ser His Glu Lys Ser
             35                  40                  45

Leu Gly Glu Ala Asp Lys Ala Asp Val Asn Val Leu Thr Lys Ala Lys
     50                  55                  60

Ser Gln
 65
```

<210> SEQ ID NO 20
<211> LENGTH: 65
<212> TYPE: PRT
<213> ORGANISM: Homo sapiens
<220> FEATURE:
<221> NAME/KEY: PEPTIDE
<222> LOCATION: (1)...(65)
<223> OTHER INFORMATION: human parathyroid hormone peptide fragment

<400> SEQUENCE: 20

```
Arg Val Glu Trp Leu Arg Lys Lys Leu Gln Asp Val His Asn Phe Val
 1               5                  10                  15

Ala Leu Gly Ala Pro Leu Ala Pro Arg Asp Ala Gly Ser Gln Arg Pro
             20                  25                  30

Arg Lys Lys Glu Asp Asn Val Leu Val Glu Ser His Glu Lys Ser Leu
             35                  40                  45

Gly Glu Ala Asp Lys Ala Asp Val Asn Val Leu Thr Lys Ala Lys Ser
     50                  55                  60

Gln
 65
```

<210> SEQ ID NO 21
<211> LENGTH: 64
<212> TYPE: PRT
<213> ORGANISM: Homo sapiens
<220> FEATURE:
<221> NAME/KEY: PEPTIDE
<222> LOCATION: (1)...(64)
<223> OTHER INFORMATION: human parathyroid hormone peptide fragment

<400> SEQUENCE: 21

```
Val Glu Trp Leu Arg Lys Lys Leu Gln Asp Val His Asn Phe Val Ala
 1               5                  10                  15

Leu Gly Ala Pro Leu Ala Pro Arg Asp Ala Gly Ser Gln Arg Pro Arg
             20                  25                  30

Lys Lys Glu Asp Asn Val Leu Val Glu Ser His Glu Lys Ser Leu Gly
             35                  40                  45

Glu Ala Asp Lys Ala Asp Val Asn Val Leu Thr Lys Ala Lys Ser Gln
     50                  55                  60
```

<210> SEQ ID NO 22
<211> LENGTH: 63
<212> TYPE: PRT
<213> ORGANISM: Homo sapiens
<220> FEATURE:
<221> NAME/KEY: PEPTIDE
<222> LOCATION: (1)...(63)
<223> OTHER INFORMATION: human parathyroid hormone peptide fragment

```
<400> SEQUENCE: 22

Glu Trp Leu Arg Lys Lys Leu Gln Asp Val His Asn Phe Val Ala Leu
1               5                   10                  15

Gly Ala Pro Leu Ala Pro Arg Asp Ala Gly Ser Gln Arg Pro Arg Lys
            20                  25                  30

Lys Glu Asp Asn Val Leu Val Glu Ser His Glu Lys Ser Leu Gly Glu
        35                  40                  45

Ala Asp Lys Ala Asp Val Asn Val Leu Thr Lys Ala Lys Ser Gln
    50                  55                  60

<210> SEQ ID NO 23
<211> LENGTH: 62
<212> TYPE: PRT
<213> ORGANISM: Homo sapiens
<220> FEATURE:
<221> NAME/KEY: PEPTIDE
<222> LOCATION: (1)...(62)
<223> OTHER INFORMATION: human parathyroid hormone peptide fragment

<400> SEQUENCE: 23

Trp Leu Arg Lys Lys Leu Gln Asp Val His Asn Phe Val Ala Leu Gly
1               5                   10                  15

Ala Pro Leu Ala Pro Arg Asp Ala Gly Ser Gln Arg Pro Arg Lys Lys
            20                  25                  30

Glu Asp Asn Val Leu Val Glu Ser His Glu Lys Ser Leu Gly Glu Ala
        35                  40                  45

Asp Lys Ala Asp Val Asn Val Leu Thr Lys Ala Lys Ser Gln
    50                  55                  60

<210> SEQ ID NO 24
<211> LENGTH: 61
<212> TYPE: PRT
<213> ORGANISM: Homo sapiens
<220> FEATURE:
<221> NAME/KEY: PEPTIDE
<222> LOCATION: (1)...(61)
<223> OTHER INFORMATION: human parathyroid hormone peptide fragment

<400> SEQUENCE: 24

Leu Arg Lys Lys Leu Gln Asp Val His Asn Phe Val Ala Leu Gly Ala
1               5                   10                  15

Pro Leu Ala Pro Arg Asp Ala Gly Ser Gln Arg Pro Arg Lys Lys Glu
            20                  25                  30

Asp Asn Val Leu Val Glu Ser His Glu Lys Ser Leu Gly Glu Ala Asp
        35                  40                  45

Lys Ala Asp Val Asn Val Leu Thr Lys Ala Lys Ser Gln
    50                  55                  60

<210> SEQ ID NO 25
<211> LENGTH: 60
<212> TYPE: PRT
<213> ORGANISM: Homo sapiens
<220> FEATURE:
<221> NAME/KEY: PEPTIDE
<222> LOCATION: (1)...(60)
<223> OTHER INFORMATION: human parathyroid hormone peptide fragment

<400> SEQUENCE: 25

Arg Lys Lys Leu Gln Asp Val His Asn Phe Val Ala Leu Gly Ala Pro
1               5                   10                  15
```

-continued

Leu Ala Pro Arg Asp Ala Gly Ser Gln Arg Pro Arg Lys Lys Glu Asp
            20                  25                  30

Asn Val Leu Val Glu Ser His Glu Lys Ser Leu Gly Glu Ala Asp Lys
        35                  40                  45

Ala Asp Val Asn Val Leu Thr Lys Ala Lys Ser Gln
    50                  55                  60

<210> SEQ ID NO 26
<211> LENGTH: 59
<212> TYPE: PRT
<213> ORGANISM: Homo sapiens
<220> FEATURE:
<221> NAME/KEY: PEPTIDE
<222> LOCATION: (1)...(59)
<223> OTHER INFORMATION: human parathyroid hormone peptide fragment

<400> SEQUENCE: 26

Lys Lys Leu Gln Asp Val His Asn Phe Val Ala Leu Gly Ala Pro Leu
 1               5                  10                  15

Ala Pro Arg Asp Ala Gly Ser Gln Arg Pro Arg Lys Lys Glu Asp Asn
            20                  25                  30

Val Leu Val Glu Ser His Glu Lys Ser Leu Gly Glu Ala Asp Lys Ala
        35                  40                  45

Asp Val Asn Val Leu Thr Lys Ala Lys Ser Gln
    50                  55

<210> SEQ ID NO 27
<211> LENGTH: 58
<212> TYPE: PRT
<213> ORGANISM: Homo sapiens
<220> FEATURE:
<221> NAME/KEY: PEPTIDE
<222> LOCATION: (1)...(58)
<223> OTHER INFORMATION: human parathyroid hormone peptide fragment

<400> SEQUENCE: 27

Lys Leu Gln Asp Val His Asn Phe Val Ala Leu Gly Ala Pro Leu Ala
 1               5                  10                  15

Pro Arg Asp Ala Gly Ser Gln Arg Pro Arg Lys Lys Glu Asp Asn Val
            20                  25                  30

Leu Val Glu Ser His Glu Lys Ser Leu Gly Glu Ala Asp Lys Ala Asp
        35                  40                  45

Val Asn Val Leu Thr Lys Ala Lys Ser Gln
    50                  55

<210> SEQ ID NO 28
<211> LENGTH: 57
<212> TYPE: PRT
<213> ORGANISM: Homo sapiens
<220> FEATURE:
<221> NAME/KEY: PEPTIDE
<222> LOCATION: (1)...(57)
<223> OTHER INFORMATION: human parathyroid hormone peptide fragment

<400> SEQUENCE: 28

Leu Gln Asp Val His Asn Phe Val Ala Leu Gly Ala Pro Leu Ala Pro
 1               5                  10                  15

Arg Asp Ala Gly Ser Gln Arg Pro Arg Lys Lys Glu Asp Asn Val Leu
            20                  25                  30

Val Glu Ser His Glu Lys Ser Leu Gly Glu Ala Asp Lys Ala Asp Val
        35                  40                  45

Asn Val Leu Thr Lys Ala Lys Ser Gln
         50                  55

```
<210> SEQ ID NO 29
<211> LENGTH: 56
<212> TYPE: PRT
<213> ORGANISM: Homo sapiens
<220> FEATURE:
<221> NAME/KEY: PEPTIDE
<222> LOCATION: (1)...(56)
<223> OTHER INFORMATION: human parathyroid hormone peptide fragment

<400> SEQUENCE: 29
```

Gln Asp Val His Asn Phe Val Ala Leu Gly Ala Pro Leu Ala Pro Arg
 1               5                  10                  15

Asp Ala Gly Ser Gln Arg Pro Arg Lys Lys Glu Asp Asn Val Leu Val
             20                  25                  30

Glu Ser His Glu Lys Ser Leu Gly Glu Ala Asp Lys Ala Asp Val Asn
         35                  40                  45

Val Leu Thr Lys Ala Lys Ser Gln
     50                  55

```
<210> SEQ ID NO 30
<211> LENGTH: 55
<212> TYPE: PRT
<213> ORGANISM: Homo sapiens
<220> FEATURE:
<221> NAME/KEY: PEPTIDE
<222> LOCATION: (1)...(55)
<223> OTHER INFORMATION: human parathyroid hormone peptide fragment

<400> SEQUENCE: 30
```

Asp Val His Asn Phe Val Ala Leu Gly Ala Pro Leu Ala Pro Arg Asp
 1               5                  10                  15

Ala Gly Ser Gln Arg Pro Arg Lys Lys Glu Asp Asn Val Leu Val Glu
             20                  25                  30

Ser His Glu Lys Ser Leu Gly Glu Ala Asp Lys Ala Asp Val Asn Val
         35                  40                  45

Leu Thr Lys Ala Lys Ser Gln
     50                  55

```
<210> SEQ ID NO 31
<211> LENGTH: 54
<212> TYPE: PRT
<213> ORGANISM: Homo sapiens
<220> FEATURE:
<221> NAME/KEY: PEPTIDE
<222> LOCATION: (1)...(54)
<223> OTHER INFORMATION: human parathyroid hormone peptide fragment

<400> SEQUENCE: 31
```

Val His Asn Phe Val Ala Leu Gly Ala Pro Leu Ala Pro Arg Asp Ala
 1               5                  10                  15

Gly Ser Gln Arg Pro Arg Lys Lys Glu Asp Asn Val Leu Val Glu Ser
             20                  25                  30

His Glu Lys Ser Leu Gly Glu Ala Asp Lys Ala Asp Val Asn Val Leu
         35                  40                  45

Thr Lys Ala Lys Ser Gln
     50

```
<210> SEQ ID NO 32
<211> LENGTH: 53
<212> TYPE: PRT
```

```
<213> ORGANISM: Homo sapiens
<220> FEATURE:
<221> NAME/KEY: PEPTIDE
<222> LOCATION: (1)...(53)
<223> OTHER INFORMATION: human parathyroid hormone peptide fragment

<400> SEQUENCE: 32

His Asn Phe Val Ala Leu Gly Ala Pro Leu Ala Pro Arg Asp Ala Gly
 1               5                   10                  15

Ser Gln Arg Pro Arg Lys Lys Glu Asp Asn Val Leu Val Glu Ser His
            20                  25                  30

Glu Lys Ser Leu Gly Glu Ala Asp Lys Ala Asp Val Asn Val Leu Thr
        35                  40                  45

Lys Ala Lys Ser Gln
        50

<210> SEQ ID NO 33
<211> LENGTH: 52
<212> TYPE: PRT
<213> ORGANISM: Homo sapiens
<220> FEATURE:
<221> NAME/KEY: PEPTIDE
<222> LOCATION: (1)...(52)
<223> OTHER INFORMATION: human parathyroid hormone peptide fragment

<400> SEQUENCE: 33

Asn Phe Val Ala Leu Gly Ala Pro Leu Ala Pro Arg Asp Ala Gly Ser
 1               5                   10                  15

Gln Arg Pro Arg Lys Lys Glu Asp Asn Val Leu Val Glu Ser His Glu
            20                  25                  30

Lys Ser Leu Gly Glu Ala Asp Lys Ala Asp Val Asn Val Leu Thr Lys
        35                  40                  45

Ala Lys Ser Gln
        50

<210> SEQ ID NO 34
<211> LENGTH: 63
<212> TYPE: PRT
<213> ORGANISM: Homo sapiens
<220> FEATURE:
<221> NAME/KEY: PEPTIDE
<222> LOCATION: (1)...(63)
<223> OTHER INFORMATION: human parathyroid hormone peptide fragment

<400> SEQUENCE: 34

Leu Met His Asn Leu Gly Lys His Leu Asn Ser Met Glu Arg Val Glu
 1               5                   10                  15

Trp Leu Arg Lys Lys Leu Gln Asp Val His Asn Phe Val Ala Leu Gly
            20                  25                  30

Ala Pro Leu Ala Pro Arg Asp Ala Gly Ser Gln Arg Pro Arg Lys Lys
        35                  40                  45

Glu Asp Asn Val Leu Val Glu Ser His Glu Lys Ser Leu Gly Glu
    50                  55                  60

<210> SEQ ID NO 35
<211> LENGTH: 64
<212> TYPE: PRT
<213> ORGANISM: Homo sapiens
<220> FEATURE:
<221> NAME/KEY: PEPTIDE
<222> LOCATION: (1)...(64)
<223> OTHER INFORMATION: human parathyroid hormone peptide fragment

<400> SEQUENCE: 35
```

```
Leu Met His Asn Leu Gly Lys His Leu Asn Ser Met Glu Arg Val Glu
 1               5                  10                  15

Trp Leu Arg Lys Lys Leu Gln Asp Val His Asn Phe Val Ala Leu Gly
            20                  25                  30

Ala Pro Leu Ala Pro Arg Asp Ala Gly Ser Gln Arg Pro Arg Lys Lys
            35                  40                  45

Glu Asp Asn Val Leu Val Glu Ser His Glu Lys Ser Leu Gly Glu Ala
    50                  55                  60
```

<210> SEQ ID NO 36
<211> LENGTH: 65
<212> TYPE: PRT
<213> ORGANISM: Homo sapiens
<220> FEATURE:
<221> NAME/KEY: PEPTIDE
<222> LOCATION: (1)...(65)
<223> OTHER INFORMATION: human parathyroid hormone peptide fragment

<400> SEQUENCE: 36

```
Leu Met His Asn Leu Gly Lys His Leu Asn Ser Met Glu Arg Val Glu
 1               5                  10                  15

Trp Leu Arg Lys Lys Leu Gln Asp Val His Asn Phe Val Ala Leu Gly
            20                  25                  30

Ala Pro Leu Ala Pro Arg Asp Ala Gly Ser Gln Arg Pro Arg Lys Lys
            35                  40                  45

Glu Asp Asn Val Leu Val Glu Ser His Glu Lys Ser Leu Gly Glu Ala
    50                  55                  60

Asp
65
```

<210> SEQ ID NO 37
<211> LENGTH: 66
<212> TYPE: PRT
<213> ORGANISM: Homo sapiens
<220> FEATURE:
<221> NAME/KEY: PEPTIDE
<222> LOCATION: (1)...(66)
<223> OTHER INFORMATION: human parathyroid hormone peptide fragment

<400> SEQUENCE: 37

```
Leu Met His Asn Leu Gly Lys His Leu Asn Ser Met Glu Arg Val Glu
 1               5                  10                  15

Trp Leu Arg Lys Lys Leu Gln Asp Val His Asn Phe Val Ala Leu Gly
            20                  25                  30

Ala Pro Leu Ala Pro Arg Asp Ala Gly Ser Gln Arg Pro Arg Lys Lys
            35                  40                  45

Glu Asp Asn Val Leu Val Glu Ser His Glu Lys Ser Leu Gly Glu Ala
    50                  55                  60

Asp Lys
65
```

<210> SEQ ID NO 38
<211> LENGTH: 67
<212> TYPE: PRT
<213> ORGANISM: Homo sapiens
<220> FEATURE:
<221> NAME/KEY: PEPTIDE
<222> LOCATION: (1)...(67)
<223> OTHER INFORMATION: human parathyroid hormone peptide fragment

<400> SEQUENCE: 38

```
Leu Met His Asn Leu Gly Lys His Leu Asn Ser Met Glu Arg Val Glu
 1               5                  10                  15

Trp Leu Arg Lys Lys Leu Gln Asp Val His Asn Phe Val Ala Leu Gly
            20                  25                  30

Ala Pro Leu Ala Pro Arg Asp Ala Gly Ser Gln Arg Pro Arg Lys Lys
            35                  40                  45

Glu Asp Asn Val Leu Val Glu Ser His Glu Lys Ser Leu Gly Glu Ala
     50                  55                  60

Asp Lys Ala
 65

<210> SEQ ID NO 39
<211> LENGTH: 68
<212> TYPE: PRT
<213> ORGANISM: Homo sapiens
<220> FEATURE:
<221> NAME/KEY: PEPTIDE
<222> LOCATION: (1)...(68)
<223> OTHER INFORMATION: human parathyroid hormone peptide fragment

<400> SEQUENCE: 39

Leu Met His Asn Leu Gly Lys His Leu Asn Ser Met Glu Arg Val Glu
 1               5                  10                  15

Trp Leu Arg Lys Lys Leu Gln Asp Val His Asn Phe Val Ala Leu Gly
            20                  25                  30

Ala Pro Leu Ala Pro Arg Asp Ala Gly Ser Gln Arg Pro Arg Lys Lys
            35                  40                  45

Glu Asp Asn Val Leu Val Glu Ser His Glu Lys Ser Leu Gly Glu Ala
     50                  55                  60

Asp Lys Ala Asp
 65

<210> SEQ ID NO 40
<211> LENGTH: 69
<212> TYPE: PRT
<213> ORGANISM: Homo sapiens
<220> FEATURE:
<221> NAME/KEY: PEPTIDE
<222> LOCATION: (1)...(69)
<223> OTHER INFORMATION: human parathyroid hormone peptide fragment

<400> SEQUENCE: 40

Leu Met His Asn Leu Gly Lys His Leu Asn Ser Met Glu Arg Val Glu
 1               5                  10                  15

Trp Leu Arg Lys Lys Leu Gln Asp Val His Asn Phe Val Ala Leu Gly
            20                  25                  30

Ala Pro Leu Ala Pro Arg Asp Ala Gly Ser Gln Arg Pro Arg Lys Lys
            35                  40                  45

Glu Asp Asn Val Leu Val Glu Ser His Glu Lys Ser Leu Gly Glu Ala
     50                  55                  60

Asp Lys Ala Asp Val
 65

<210> SEQ ID NO 41
<211> LENGTH: 70
<212> TYPE: PRT
<213> ORGANISM: Homo sapiens
<220> FEATURE:
<221> NAME/KEY: PEPTIDE
<222> LOCATION: (1)...(70)
<223> OTHER INFORMATION: human parathyroid hormone peptide fragment
```

-continued

<400> SEQUENCE: 41

Leu Met His Asn Leu Gly Lys His Leu Asn Ser Met Glu Arg Val Glu
1               5                   10                  15

Trp Leu Arg Lys Lys Leu Gln Asp Val His Asn Phe Val Ala Leu Gly
            20                  25                  30

Ala Pro Leu Ala Pro Arg Asp Ala Gly Ser Gln Arg Pro Arg Lys Lys
        35                  40                  45

Glu Asp Asn Val Leu Val Glu Ser His Glu Lys Ser Leu Gly Glu Ala
    50                  55                  60

Asp Lys Ala Asp Val Asn
65                  70

<210> SEQ ID NO 42
<211> LENGTH: 71
<212> TYPE: PRT
<213> ORGANISM: Homo sapiens
<220> FEATURE:
<221> NAME/KEY: PEPTIDE
<222> LOCATION: (1)...(71)
<223> OTHER INFORMATION: human parathyroid hormone peptide fragment

<400> SEQUENCE: 42

Leu Met His Asn Leu Gly Lys His Leu Asn Ser Met Glu Arg Val Glu
1               5                   10                  15

Trp Leu Arg Lys Lys Leu Gln Asp Val His Asn Phe Val Ala Leu Gly
            20                  25                  30

Ala Pro Leu Ala Pro Arg Asp Ala Gly Ser Gln Arg Pro Arg Lys Lys
        35                  40                  45

Glu Asp Asn Val Leu Val Glu Ser His Glu Lys Ser Leu Gly Glu Ala
    50                  55                  60

Asp Lys Ala Asp Val Asn Val
65                  70

<210> SEQ ID NO 43
<211> LENGTH: 72
<212> TYPE: PRT
<213> ORGANISM: Homo sapiens
<220> FEATURE:
<221> NAME/KEY: PEPTIDE
<222> LOCATION: (1)...(72)
<223> OTHER INFORMATION: human parathyroid hormone peptide fragment

<400> SEQUENCE: 43

Leu Met His Asn Leu Gly Lys His Leu Asn Ser Met Glu Arg Val Glu
1               5                   10                  15

Trp Leu Arg Lys Lys Leu Gln Asp Val His Asn Phe Val Ala Leu Gly
            20                  25                  30

Ala Pro Leu Ala Pro Arg Asp Ala Gly Ser Gln Arg Pro Arg Lys Lys
        35                  40                  45

Glu Asp Asn Val Leu Val Glu Ser His Glu Lys Ser Leu Gly Glu Ala
    50                  55                  60

Asp Lys Ala Asp Val Asn Val Leu
65                  70

<210> SEQ ID NO 44
<211> LENGTH: 73
<212> TYPE: PRT
<213> ORGANISM: Homo sapiens
<220> FEATURE:
<221> NAME/KEY: PEPTIDE
<222> LOCATION: (1)...(73)

-continued

<223> OTHER INFORMATION: human parathyroid hormone peptide fragment

<400> SEQUENCE: 44

Leu Met His Asn Leu Gly Lys His Leu Asn Ser Met Glu Arg Val Glu
 1               5                  10                  15

Trp Leu Arg Lys Lys Leu Gln Asp Val His Asn Phe Val Ala Leu Gly
            20                  25                  30

Ala Pro Leu Ala Pro Arg Asp Ala Gly Ser Gln Arg Pro Arg Lys Lys
        35                  40                  45

Glu Asp Asn Val Leu Val Glu Ser His Glu Lys Ser Leu Gly Glu Ala
    50                  55                  60

Asp Lys Ala Asp Val Asn Val Leu Thr
65                  70

<210> SEQ ID NO 45
<211> LENGTH: 74
<212> TYPE: PRT
<213> ORGANISM: Homo sapiens
<220> FEATURE:
<221> NAME/KEY: PEPTIDE
<222> LOCATION: (1)...(74)
<223> OTHER INFORMATION: human parathyroid hormone peptide fragment

<400> SEQUENCE: 45

Leu Met His Asn Leu Gly Lys His Leu Asn Ser Met Glu Arg Val Glu
 1               5                  10                  15

Trp Leu Arg Lys Lys Leu Gln Asp Val His Asn Phe Val Ala Leu Gly
            20                  25                  30

Ala Pro Leu Ala Pro Arg Asp Ala Gly Ser Gln Arg Pro Arg Lys Lys
        35                  40                  45

Glu Asp Asn Val Leu Val Glu Ser His Glu Lys Ser Leu Gly Glu Ala
    50                  55                  60

Asp Lys Ala Asp Val Asn Val Leu Thr Lys
65                  70

<210> SEQ ID NO 46
<211> LENGTH: 75
<212> TYPE: PRT
<213> ORGANISM: Homo sapiens
<220> FEATURE:
<221> NAME/KEY: PEPTIDE
<222> LOCATION: (1)...(75)
<223> OTHER INFORMATION: human parathyroid hormone peptide fragment

<400> SEQUENCE: 46

Leu Met His Asn Leu Gly Lys His Leu Asn Ser Met Glu Arg Val Glu
 1               5                  10                  15

Trp Leu Arg Lys Lys Leu Gln Asp Val His Asn Phe Val Ala Leu Gly
            20                  25                  30

Ala Pro Leu Ala Pro Arg Asp Ala Gly Ser Gln Arg Pro Arg Lys Lys
        35                  40                  45

Glu Asp Asn Val Leu Val Glu Ser His Glu Lys Ser Leu Gly Glu Ala
    50                  55                  60

Asp Lys Ala Asp Val Asn Val Leu Thr Lys Ala
65                  70                  75

<210> SEQ ID NO 47
<211> LENGTH: 76
<212> TYPE: PRT
<213> ORGANISM: Homo sapiens
<220> FEATURE:

-continued

```
<221> NAME/KEY: PEPTIDE
<222> LOCATION: (1)...(76)
<223> OTHER INFORMATION: human parathyroid hormone peptide fragment

<400> SEQUENCE: 47

Leu Met His Asn Leu Gly Lys His Leu Asn Ser Met Glu Arg Val Glu
 1               5                  10                  15

Trp Leu Arg Lys Lys Leu Gln Asp Val His Asn Phe Val Ala Leu Gly
            20                  25                  30

Ala Pro Leu Ala Pro Arg Asp Ala Gly Ser Gln Arg Pro Arg Lys Lys
        35                  40                  45

Glu Asp Asn Val Leu Val Glu Ser His Glu Lys Ser Leu Gly Glu Ala
    50                  55                  60

Asp Lys Ala Asp Val Asn Val Leu Thr Lys Ala Lys
65                  70                  75

<210> SEQ ID NO 48
<211> LENGTH: 77
<212> TYPE: PRT
<213> ORGANISM: Homo sapiens
<220> FEATURE:
<221> NAME/KEY: PEPTIDE
<222> LOCATION: (1)...(77)
<223> OTHER INFORMATION: human parathyroid hormone peptide fragment

<400> SEQUENCE: 48

Leu Met His Asn Leu Gly Lys His Leu Asn Ser Met Glu Arg Val Glu
 1               5                  10                  15

Trp Leu Arg Lys Lys Leu Gln Asp Val His Asn Phe Val Ala Leu Gly
            20                  25                  30

Ala Pro Leu Ala Pro Arg Asp Ala Gly Ser Gln Arg Pro Arg Lys Lys
        35                  40                  45

Glu Asp Asn Val Leu Val Glu Ser His Glu Lys Ser Leu Gly Glu Ala
    50                  55                  60

Asp Lys Ala Asp Val Asn Val Leu Thr Lys Ala Lys Ser
65                  70                  75
```